United States Patent [19]

Sela et al.

[11] Patent Number: 6,066,621
[45] Date of Patent: May 23, 2000

[54] SYNTHETIC PEPTIDES FOR THE TREATMENT OF MYASTHENIA GRAVIS

[75] Inventors: Michael Sela; Edna Mozes, both of Rehovot, Israel

[73] Assignee: Yeda Research and Development Co. Ltd., Rehovot, Israel

[21] Appl. No.: 08/475,577

[22] Filed: Jun. 7, 1995

Related U.S. Application Data

[63] Continuation-in-part of application No. 08/096,909, Jul. 26, 1993, abandoned, which is a continuation-in-part of application No. 07/900,393, Jun. 18, 1992, abandoned, which is a continuation-in-part of application No. 07/624,730, Dec. 10, 1990, Pat. No. 5,356,779.

[51] Int. Cl.$^7$ .................................................. A61K 38/00
[52] U.S. Cl. ................................. 514/15; 514/12; 514/13; 514/14; 530/324; 530/325; 530/326; 530/329; 530/328; 530/403
[58] Field of Search ..................................... 435/7.2, 7.21, 435/7.24; 36/501, 506, 86, 403; 530/300, 328, 324, 325, 326, 327; 514/12, 13, 14, 15; 574/15

[56] References Cited

U.S. PATENT DOCUMENTS 5,116,944  5/1992  Sivam et al. ............................. 530/362

FOREIGN PATENT DOCUMENTS 0304279  2/1989  European Pat. Off. .
0432691  6/1991  European Pat. Off. .
WO94/00148  1/1994  WIPO .

OTHER PUBLICATIONS

Wraith et al., Cell, 59: 247–255, Oct. 1989.
Tisch et al., Proc. Natl. Acad. Sci. USA, 91: 437–438, Jan. 1994.
Urban et al. Cell vol. 59:257–271, 1989.
Brocke et al. J.C.I. vol. 82:1894–1900, 1988.
Janeway. Nature. vol. 341: 482–483, 1989.
Zisman et al, "Peptide analogs to pathogoenic epitopes of the human acetylcholine receptor alpha subunit as potential modulators of myasthenia gravis", *Proc. Natl. Acad. Sci. USA*, 93:4492–4497 Apr. 1996.
Roit, I.M. *Essential Immunology*, 5th Edition, Blackwell Scientific Publications, Oxoford, UK, 1984, pp. 65–66.
Rothbard, J.B. et al., *International Immunology*, 11, 479–486, 1989.
Mozes, E. et al., *EMBO Journal*, 8, 4049–4052 (1989).
Smilek, D.E. et al., *Immunol. Rev.*, 118, 37–71 (1990).
Busch, R. et al., *International Immunology*, 2, 444–451 (1990).
Chemical Abstracts, vol. 112, No. 19, May 1990, p. 537, abstr. No. 176542y, Columbus, OH; E. Mozes et al, "Direct binding of a myasthenia gravis related epitope to MHC class II molecules on murine antigen–presenting cells," & EMBO. J. 1989, 8(13), 4049–2.

Ceppellini, R. et al., "Binding of labelled influenza matric peptide to HLA DR in living B1 Lymphoid cells", *Nature*, vol. 339, Jun. 1989, pp. 392–394.
Budmer et al., *Immunology*, 66(2):163–169, 1989.
Sakai, K. et al., "Prevention of experimental encephalomyelitis with peptides that block interaction of T cells with major histocompatibility complex proteins", *Proc. Natl. Acad. Sci. USA*, vol. 86, pp. 9470–9474, (1989).
Urban, James et al., "Autoimmune T Cells: Immune Recognition of Normal and Variant Peptide Epitopes and Peptide–Based Therapy", *Cell*, vol. 59, Oct. 20, 1989, pp. 257–271.
Lindstrom, et al., *Advances in Immunology*, 42:233–284, 1988.
Lopez et al., *J. Exp. Med*, 170(1): 203–215, 1989.
Pola et al., *J. Immunology*, 141(7): 2289–2294, 1988.
Wraith et al., "Antigen Recognition in Autoimmune Encephalomyelitis and the Potential for Peptide–Meidated Immunotherapy", *Cell*, 59, pp. 247–255 (1989).
Wraith et al., "T cell recognition as the target for Immune Intervention in Autoimmune Diseases", *Cell*, 557, pp. 709–715, (1989).
Brocke et al., "In Vitro Proliferative Responses and Antibody Titers Specific to Human Acetylcholine Receptor Synthetic Peptides in Patients with Myasthenia Gravis and Relation to HLA Class II Genes", *J. Clin. Invest.*, 82:1894–1900 (1988).
Madden et al., "The structure of HLA–B27 reveals nomamer self–peptides bound in an extended conformation", *Nature*, 353:321–325 (1991).
Katz–Levey et al., "Inhibition of T–cell reactivity to myasthenogenic epitopes of the human acetylcholine receptor by synthetic analogs", *Proc. Natl. Acad. Sci.*, 90:7000–7004 (Aug. 1993).
Brocke et al., "Inhibition of T cell proliferation specific for acetylcholine receptor epitopes related to myasthenia gravis with antibody to T cell receptor or with competitive syntheitc polymers", *International Immunology*, 2, #8, pp. 735–742(1990).
Plattner et al., "Obstacles to drug developement from peptide leads", pp. 92–126 in *Drug Discovery Techniques*, Clark et al., editor, Ellis Harwood Ltd. (1990).
Kirshner et al., "Altered Peptide Ligands of a Myasthenogenic Epitope as Modulators of Specific T–Cell Responses", *Scand. J. Immunol.*, 44:512–521, 1996.

(List continued on next page.)

*Primary Examiner*—Christina Y. Chan
*Assistant Examiner*—Patrick J. Nolan
*Attorney, Agent, or Firm*—Browdy and Neimark

[57] ABSTRACT

Peptides having at least nine amino acid residues each including an amino acid sequence which corresponds to position p200-208 or p262-266 of the human acetylcholine receptor α-subunit, but differing therefrom by one or more amino acid substitutions, are disclosed. These peptides inhibit the proliferative response of human peripheral blood lymphocytes to the myasthenogenic peptides p195-212 and p259-271 and are suitable for treatment of subjects afflicted with myasthenia gravis.

37 Claims, 10 Drawing Sheets

OTHER PUBLICATIONS

Zisman et al., "Binding of Peptides of the Human Acetylcholine Receptor α–Subunit to HLA Class II of Patients with Myastenia Gravis", *Human Immunology*, 44:121–130 (1995).

Kirshner et al., "Fine Specificity of T Cell Lines and Clones That Are Capable of Inducing Autoimmune Manifestations in Mice", *Cellular Immunology*, 157:11–28 (1994).

Brocke et al., "The autoimmune response of different mouse strains to T–cell epitopes of the human acetylcholine receptor α subunit", *Immunology*, 69:495–500, 1990.

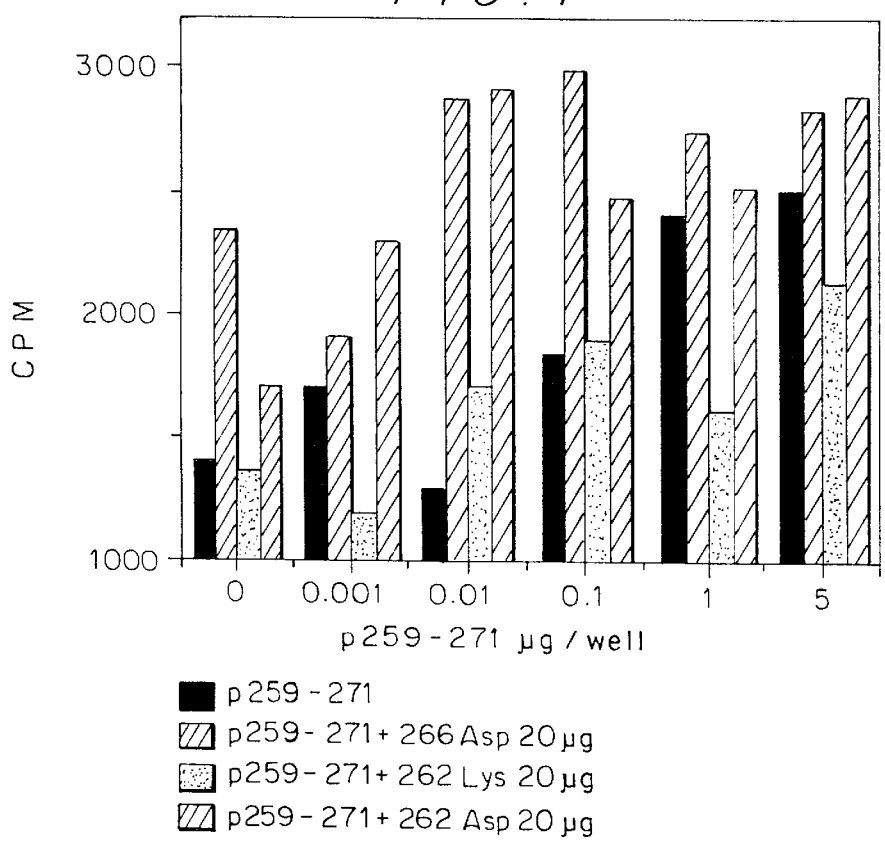
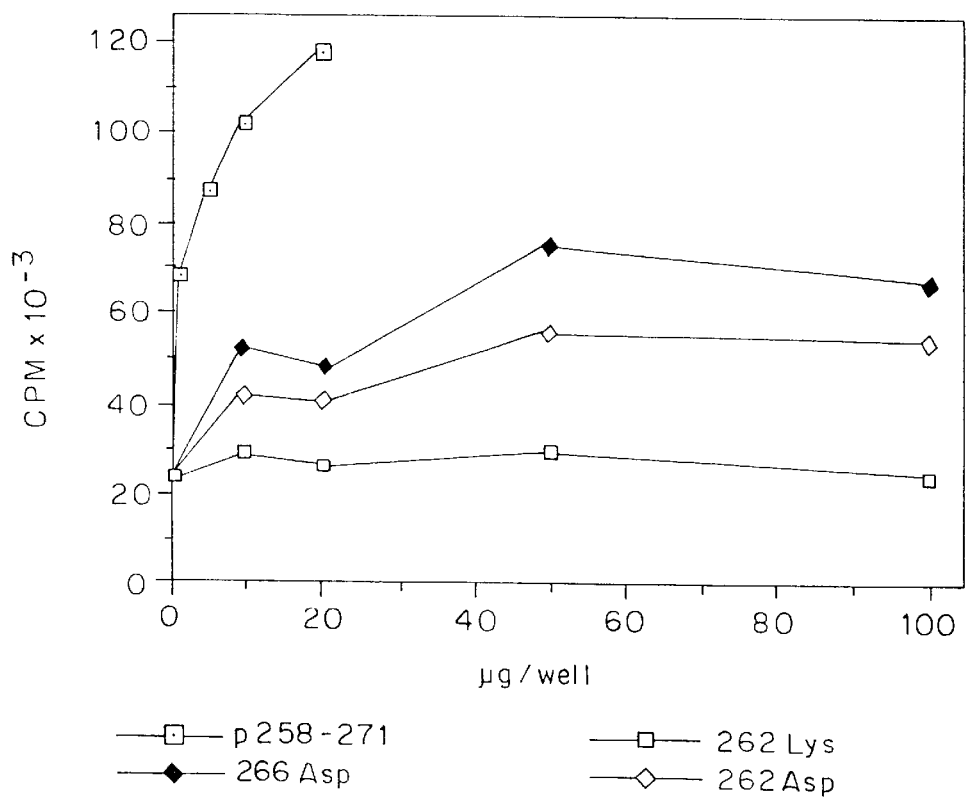

FIG. 8A

Analogs of p195-212

| | | | | | | | | | | | | | | | | | | | SEQ ID NO: |
|---|---|---|---|---|---|---|---|---|---|---|---|---|---|---|---|---|---|---|---|
| p195-212 | D | T | P | Y | L | D | I | T | Y | H | F | V | M | Q | R | L | P | L | 1 |
| 200Lys | - | - | - | - | - | K | - | - | - | - | - | - | - | - | - | - | - | - | 3 |
| 203Phe | - | - | - | - | - | - | - | - | F | - | - | - | - | - | - | - | - | - | 4 |
| 204Gly | - | - | - | - | - | - | - | - | - | G | - | - | - | - | - | - | - | - | 5 |
| 207Ala | - | - | - | - | - | - | - | - | - | - | - | - | A | - | - | - | - | - | 6 |
| 208Asp | - | - | - | - | - | - | - | - | - | - | - | - | - | D | - | - | - | - | 7 |
| 208Asn | - | - | - | - | - | - | - | - | - | - | - | - | - | N | - | - | - | - | 8 |
| 209Lys | - | - | - | - | - | - | - | - | - | - | - | - | - | - | K | - | - | - | 9 |

FIG. 8B

Analogs of p259-271

| | | | | | | | | | | | | | | SEQ ID NO: |
|---|---|---|---|---|---|---|---|---|---|---|---|---|---|---|
| p259-271 | V | I | V | E | L | I | P | S | T | S | S | A | V | 2 |
| 262Asp | - | - | - | D | - | - | - | - | - | - | - | - | - | 10 |
| 262Lys | - | - | - | K | - | - | - | - | - | - | - | - | - | 11 |
| 262Ser | - | - | - | S | - | - | - | - | - | - | - | - | - | 12 |
| 265Ala | - | - | - | - | - | - | A | - | - | - | - | - | - | 13 |
| 265Leu | - | - | - | - | - | - | L | - | - | - | - | - | - | 14 |
| 265Phe | - | - | - | - | - | - | F | - | - | - | - | - | - | 15 |
| 266Asp | - | - | - | - | - | - | - | D | - | - | - | - | - | 16 |

FIG. 8C

207Ala-262Lys -

D T P Y L D I T Y H F V A Q R L P L  V I V K L I P S T S S A V
(SEQ ID NO: 17)

262Lys-207Ala -

V I V K L I P S T S S A V  D T P Y L D I T Y H F V A Q R L P L
(SEQ ID NO: 18)

—□— 207 Ala - 262 Lys
----◇---- 262 Lys - 207 Ala
---○--- 262 Lys

—□— p195-212
----◇---- p195-212 + 262 Lys-207 Ala 500 μg / mouse per os
---○--- p195-212 + 262 Lys-207 Ala 250 μg / mouse per os
--△-- p195-212 + 262 Lys-207 Ala 200 μg / mouse i.p.
--□-- p195-212 + 262 Lys-207 Ala 200 μg / mouse i.v.

```
                          SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
          (A) LENGTH: 18 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:1:

Asp Thr Pro Tyr Leu Asp Ile Thr Tyr His Phe Val Met Gln Arg Leu
1               5                  10                  15

Pro Leu (2) INFORMATION FOR SEQ ID NO:2:

(i) SEQUENCE CHARACTERISTICS:
          (A) LENGTH: 13 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:2:

Val Ile Val Glu Leu Ile Pro Ser Thr Ser Ser Ala Val
1               5                  10

(2) INFORMATION FOR SEQ ID NO:3:

(i) SEQUENCE CHARACTERISTICS:
          (A) LENGTH: 18 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:3:

Asp Thr Pro Tyr Leu Lys Ile Thr Tyr His Phe Val Met Gln Arg Leu
1               5                  10                  15

Pro Leu (2) INFORMATION FOR SEQ ID NO:4:

(i) SEQUENCE CHARACTERISTICS:
          (A) LENGTH: 18 amino acids
          (B) TYPE: amino acid
          (C) STRANDEDNESS: single
          (D) TOPOLOGY: linear
```

(ii) MOLECULE TYPE: peptide (xi) SEQUENCE DESCRIPTION: SEQ ID NO:4:

Asp Thr Pro Tyr Leu Asp Ile Thr Phe His Phe Val Met Gln Arg Leu
1               5                  10                  15

Pro Leu (2) INFORMATION FOR SEQ ID NO:5:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:5:

Asp Thr Pro Tyr Leu Asp Ile Thr Tyr Gly Phe Val Met Gln Arg Leu
1               5                  10                  15

Pro Leu (2) INFORMATION FOR SEQ ID NO:6:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:6:

Asp Thr Pro Tyr Leu Asp Ile Thr Tyr His Phe Val Ala Gln Arg Leu
1               5                  10                  15

Pro Leu (2) INFORMATION FOR SEQ ID NO:7:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:7:

Asp Thr Pro Tyr Leu Asp Ile Thr Tyr His Phe Val Met Asp Arg Leu
1               5                  10                  15

Pro Leu (2) INFORMATION FOR SEQ ID NO:8:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:8:

Asp Thr Pro Tyr Leu Asp Ile Thr Tyr His Phe Val Met Asn Arg Leu
1               5                  10                  15

Pro Leu (2) INFORMATION FOR SEQ ID NO:9:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Asp Thr Pro Tyr Leu Asp Ile Thr Tyr His Phe Val Met Gln Lys Leu
1               5                  10                  15
Pro Leu
```

(2) INFORMATION FOR SEQ ID NO:10:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Val Ile Val Asp Leu Ile Pro Ser Thr Ser Ser Ala Val
1               5                  10
```

(2) INFORMATION FOR SEQ ID NO:11:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Val Ile Val Lys Leu Ile Pro Ser Thr Ser Ser Ala Val
1               5                  10
```

(2) INFORMATION FOR SEQ ID NO:12:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

```
Val Ile Val Ser Leu Ile Pro Ser Thr Ser Ser Ala Val
1               5                  10
```

(2) INFORMATION FOR SEQ ID NO:13:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide

```
        (xi) SEQUENCE DESCRIPTION: SEQ ID NO:13:

Val Ile Val Glu Leu Ile Ala Ser Thr Ser Ser Ala Val
1               5                   10

(2) INFORMATION FOR SEQ ID NO:14:

(i) SEQUENCE CHARACTERISTICS:
         (A) LENGTH: 13 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:14:

Val Ile Val Glu Leu Ile Leu Ser Thr Ser Ser Ala Val
1               5                   10

(2) INFORMATION FOR SEQ ID NO:15:

(i) SEQUENCE CHARACTERISTICS:
         (A) LENGTH: 13 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:15:

Val Ile Val Glu Leu Ile Phe Ser Thr Ser Ser Ala Val
1               5                   10

(2) INFORMATION FOR SEQ ID NO:16:

(i) SEQUENCE CHARACTERISTICS:
         (A) LENGTH: 13 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:16:

Val Ile Val Glu Leu Ile Pro Asp Thr Ser Ser Ala Val
1               5                   10

(2) INFORMATION FOR SEQ ID NO:17:

(i) SEQUENCE CHARACTERISTICS:
         (A) LENGTH: 31 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:17:

Asp Thr Pro Tyr Leu Asp Ile Thr Tyr His Phe Val Ala Gln Arg Leu
1               5                   10                  15

Pro Leu Val Ile Val Lys Leu Ile Pro Ser Thr Ser Ser Ala Val
            20                  25                  30

(2) INFORMATION FOR SEQ ID NO:18:

(i) SEQUENCE CHARACTERISTICS:
         (A) LENGTH: 31 amino acids
         (B) TYPE: amino acid
         (C) STRANDEDNESS: single
```

-continued

```
      (D) TOPOLOGY: linear (ii) MOLECULE TYPE: peptide (xi) SEQUENCE DESCRIPTION: SEQ ID NO:18:

Val Ile Val Lys Leu Ile Pro Ser Thr Ser Ser Ala Val Asp Thr Pro
1               5                   10                  15

Tyr Leu Asp Ile Thr Tyr His Phe Val Ala Gln Arg Leu Pro Leu
            20                  25                  30
```

SYNTHETIC PEPTIDES FOR THE TREATMENT OF MYASTHENIA GRAVIS

CROSS-REFERENCE TO RELATED APPLICATIONS

The present application is a continuation-in-part of application Ser. No. 08/096,909, filed Jul. 26, 1993, now abandoned, which was a continuation-in-part of application Ser. No. 07/900,393, filed Jun. 18, 1992, now abandoned, which was a continuation-in-part of application Ser. No. 07/624,730, filed Dec. 10, 1990, now U.S. Pat. No. 5,356,779. The entire contents of each of said three prior applications are hereby incorporated herein by reference.

FIELD OF THE INVENTION

The present invention relates to synthetic peptides useful for the treatment of myasthenia gravis (MG) patients, and to pharmaceutical compositions comprising these peptides by themselves, in a combined or polymerized form, or attached to a macromolecular carrier.

DESCRIPTION OF THE BACKGROUND ART

Autoimmune diseases are characterized by immune responses that are directed against self antigens. These responses are maintained by the persistent activation of self-reactive T lymphocytes. T lymphocytes are specifically activated upon recognition of foreign and/or self antigens as a complex with self Major Histocompatibility Complex (MHC) gene products on the surface of antigen-presenting cells (APC).

Myasthenia gravis (MG) is an autoimmune disorder, the symptoms of which are caused by an antibody-mediated autoimmune attack on the acetylcholine receptor (AChR) of the post-synaptic membrane of the neuromuscular junction. This antibody attack results in loss of acetylcholine receptors and jeopardizes normal neuromuscular transmission, leading to episodic muscle weakness, chiefly in muscles innervated by cranial nerves, and to fatigability.

T lymphocytes are considered to play a central role in the autoreactive process, but the specific immunoregulatory mechanisms by which the T cells exert their regulatory role leading to the induction and various clinical manifestations of MG are poorly understood, and no specific cure is available for the treatment of myasthenic patients. Presently, treatment is with cholinesterase inhibitors, such as pyridostigmine and neostigmine, thymectomy, corticosteroids, and immuno-suppressive agents and plasmapheresis.

MG is a well defined autoimmune disorder mediated by antibodies specific to determinants of the AChR. Specific genes of the human MHC, the HLA system, were shown to be significantly associated with the disease. The high frequency of certain histocompatibility antigens (HLA-B8, DR3) in MG patients suggests a defect of immunoregulation that might be expressed on the level of T cells.

In previous studies we found that two peptides representing sequences of the human AChR α-subunit (p195-212 and p257-269) significantly stimulated peripheral blood lymphocytes (PBL) from MG patients in comparison to healthy controls (Brocke, S. et al. (1988), *J. Clin. Invest.* 82:1894–1900). In addition, a correlation was demonstrated between the HLA-DR types of the MG patients and their responses to these peptides. Thus, all patients that expressed HLA-DR3 responded to p257-269 and 83% of patients who expressed HLA-DR5 responded to p195-212.

Extension of this research using inbred mouse strains led to the identification of high, intermediate and low responder strains to the sequences p195-212 and p259-271 of the human AChR α-subunit. Furthermore, lymph node cells, from Torpedo-derived AChR immunized SJL and BALB/c mice, proliferated in response to p195-212 and p259-271, respectively, even better than to the immunizing antigen (Brocke, S. et al. (1990), *Immunol.* 69:495). These results indicate that peptides p195-212 and p259-271 are immunodominant murine T cell epitopes.

Long-term T cell lines and clones of C3H.SW origin specific to synthetic immunogenic peptides p195-212 and p259-271 were established in our laboratory and described by Brocke, S. et al. (1990a), *Internat. Immunol.* 2:735–742, herein incorporated by reference. Using these cell lines and clones, it is possible to characterize the T cell recognition process of myasthenic epitopes. Using this method, T cell lines and clones specific to p195-212 were established from lymph node cells of low (C3H.SW) and high (SJL) responder mouse strains, and T cell lines and clones specific to p259-271 were developed from lymph node cells of low (C3H.SW) and high (BALB/c) responder mouse strains.

It has recently been reported that when activated cells of these cell lines are inoculated into naive syngeneic mice, peptide-specific antibodies and antibodies to the murine acetylcholine receptor are detected. In addition, decremented compound muscle action potentials (CMAP) consistent with impairment of neuromuscular transmission are seen in the line-inoculated mice. Thus, this can serve as a marine model of MG-related autoimmune manifestations. See Kirshner et al., (1994), *Cell. Immunol.*, 157: 11–28, the entire contents of which are hereby incorporated by reference. CMAP is also used for diagnosis of MG patients.

European patent publication no. 432,691 describes an assay for the measurement of direct binding of a peptide that is a T-cell epitope to gene products of the major histocompatibility complex (MHC), classes I and II, on the surface of intact living antigen-presenting cells (APC). The assay comprises incubating the labelled peptide with the APC and monitoring the extent of binding by the addition of a probe that reacts with the ligand used to label the peptide. The assay is suitable for autoimmune diseases and other immunological disorders. With this assay it was demonstrated that p195-212 binds directly to MHC class II molecules on living APC from several different mouse strains. This observed binding capacity for the peptide was shown to correlate with the proliferative potential of the different mouse strains and was inhibited by the relevant anti-I-A antibodies. In addition, it was shown that APC from MG patients and healthy controls, who responded by proliferation to peptides p195-212 and/or p259-271, also bound the same peptides, labelled with biotin. The ability to screen peptides by their direct binding to MHC products and by their stimulatory capacity to T cells might shed light on the role of MG-related epitopes in the pathogenesis of the disease.

It has been suggested that peptide analogs obtained by amino acid substitutions in a stretch of the sequence of a peptidic antigen relevant to an autoimmune disease might lead to peptides that bind to MHC gene products but that do not stimulate specific helper T cells. Such peptides can be used to inhibit competitively T cell reactivity in vitro and in vivo and thus for treatment of the corresponding autoimmune disease (Sakai, K. et al. (1989), *PNAS* 86:9470; Urban, J. L. et al. (1989), *Cell* 59:257; European patent publication no. 432,691, and PCT publication no. WO 92/04049). However, none of the references provide any information or guidance on the amino acids of the pathogenic peptide that can be substituted and which amino acids can serve as suitable substituents, in order to obtain a peptide analog that

SUMMARY OF THE INVENTION

It is an object of the present invention to provide synthetic peptides that are analogs of myasthenogenic T cell epitopes which represent sequences of the human AChR subunit, and are designed for specific treatment of myasthenia gravis. These synthetic peptides bind to MHC Class II gene products but do not activate the T cells involved in MG-related autoimmune responses.

The invention thus relates to synthetic peptides capable of inhibiting the proliferative response of T lymphocytes from myasthenia gravis patients to a myasthenogenic peptide corresponding to a sequence of the human acetylcholine receptor α-subunit selected from the peptide p195-212 of the sequence (SEQ ID NO:1):

```
    195              200              205
    Asp-Thr-Pro-Tyr-Leu-Asp-Ile-Thr-Tyr-His-Phe-
                    210
    Val-Met-Gln-Arg-Leu-Pro-Leu
``` and the peptide p259-271 of the sequence (SEQ ID NO:2):

```
259 260              265              270
Val-Ile-Val-Glu-Leu-Ile-Pro-Ser-Thr-Ser-Ser-Ala-Val
``` said synthetic peptides having at least nine amino acid residues and differing from the peptides p195-212 and p259-271 by one or more amino acid substitutions. The invention further relates to conjugates of two or more of said synthetic peptides, either directly synthesized in tandem or connected via a spacer, as well as to polymers of said peptides and conjugates thereof with a macromolecular carrier.

The invention further relates to pharmaceutical compositions and to a method for treatment of myasthenia gravis by administration of the peptides of the invention by themselves, in a polymerized form or attached to a macromolecular carrier.

BRIEF DESCRIPTION OF THE DRAWINGS

FIG. 4 is a graph showing inhibition of the helper activity of the T cell line, TCBALB/c259-271, with various doses of the peptide p259-271 alone or in combination with each of the analogs 266Asp, 262Lys and 262Asp.

FIG. 5 is a graph showing proliferative responses of lymph node cells of BALB/c mice immunized with p259-271, to various doses of p259-271, 266Asp, 262Lys and 262Asp.

FIGS. 8A–C show the sequences and SEQ ID NOS 1–18 of the analogs of p195-212, the analogs of p259-271 and the dual epitope analogs, respectively, which were synthesized in Example 1.

DETAILED DESCRIPTION OF PREFERRED EMBODIMENTS

Figure 1:
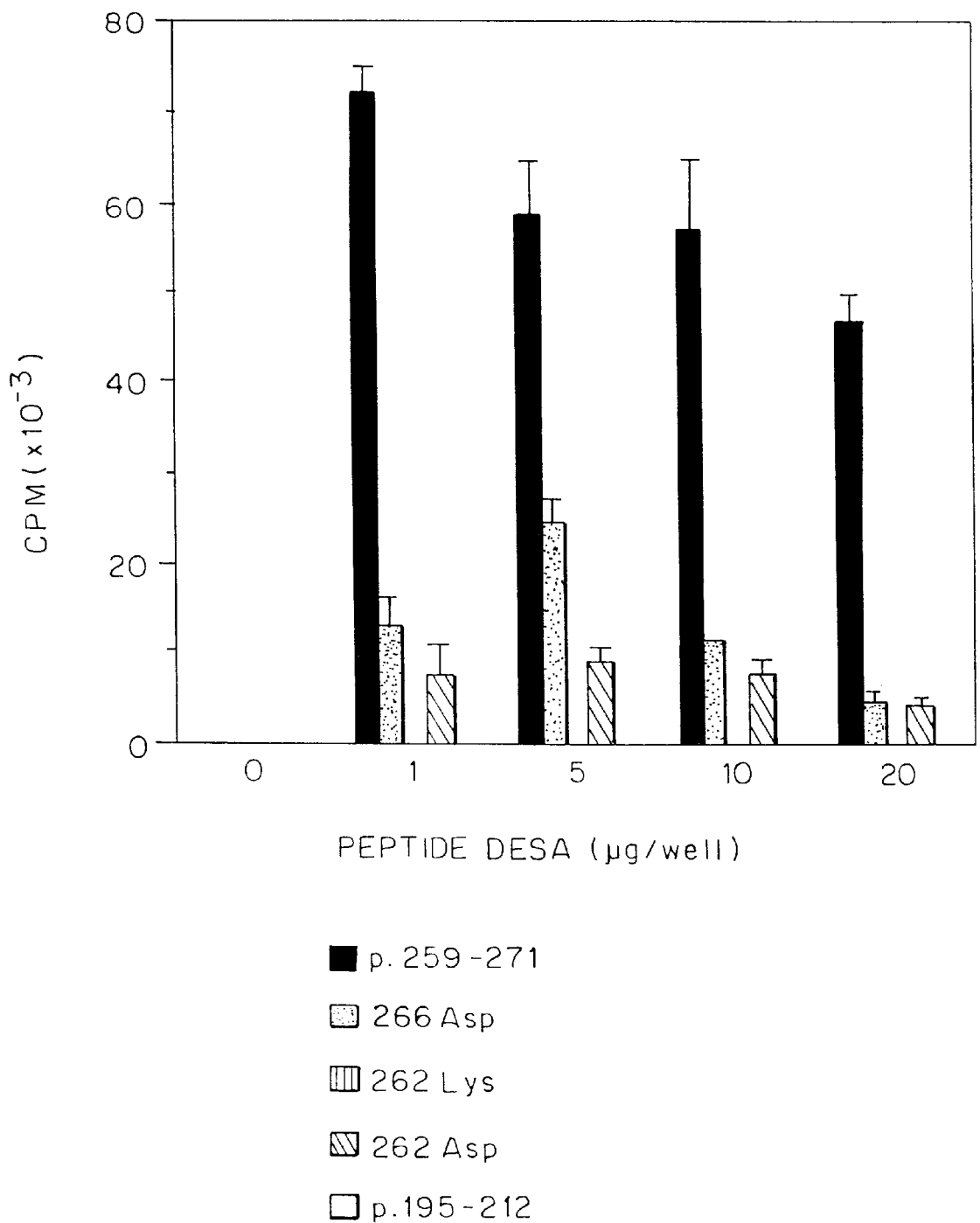
FIG. 1 is a graph showing proliferative responses of the T cell line, TCBALB/c259-271, to various doses of the myasthenogenic peptide p259-271 and its analogs 266Asp, 262Lys and 262Asp.

The present invention relates to analogs of myasthenogenic peptides p195-212 (SEQ ID NO:1) and p259-271 (SEQ ID NO:2) which will bind with high affinity to the appropriate MHC Class II molecules but will not lead to further activation of T cells. Examples of such analogs are provided, as is a procedure which may be followed by anyone of ordinary skill in the art in order to identify additional peptides which will also accomplish this function. The invention is based on the design and synthesis of peptides with amino acid substitutions at different positions that are based on parent peptides p195-212 and p259-271. By means of appropriate substitutions, analogs can be identified which are antagonists to the action of the myasthenogenic epitopes in the course of myasthenia gravis. An analog which will bind with high affinity to the appropriate MHC Class II molecules but will not lead to further activation of T cells will compete with the myasthenogenic peptides which must bind to the same MHC Class II molecules in order to cause activation of the T cells which, in turn, lead to the production of the antibodies which cause myasthenia gravis. By competing with the myasthenogenic peptides which cause T cell proliferation, the adverse effects of myasthenia gravis can be ameliorated.

It has been assumed that the portions of the myasthenogenic epitopes p195-212 and p259-271 which are most important for their function as a T cell epitope are amino acid residues 200–208 of SEQ ID NO:1 and 262–266 of SEQ ID NO:2. Thus, the changes are preferably made in these core areas. It is expected that the amino acid residues outside of these core areas are not as important to the function of binding to the appropriate MHC Class II molecules and thus it is not expected that changes in these amino acid residues will prevent further activation of the T cells. Accordingly, there is no need to change them, but if substitutions are made in the non-core amino acid residues, they should be selected to fulfill the guidelines discussed herein as to the cumulative effects of the substitutions.

Amino acids may be divided along the lines of volume, hydrophobic-hydrophilic pattern and charge. With respect to volume, those of ordinary skill in the art understand that the amino acids with the largest volume are Trp, Tyr, Phe, Arg, Lys, Ile, Leu, Met and His, while those with the smallest volumes are Gly, Ala, Ser, Asp, Thr and Pro, with others being in between.

With respect to hydrophobic-hydrophilic pattern, it is well known that the amino acids Gly, Ala, Phe, Val, Leu, Ile, Pro, Met and Trp are hydrophobic, whereas all of the remaining amino acids are hydrophilic. Among the hydrophilic amino acids, Ser, Thr, Gln and Tyr have no charge, while Arg, Lys, His and Asn have a positive charge and Asp and Glu have negative charges.

What is important in selecting peptides to be tested for their potential in inhibiting the proliferative response of T lymphocytes from a myasthenia gravis patient to the myasthenogenic peptide SEQ ID NO:1 or SEQ ID NO:2 to which it corresponds, is that the substitutions be selected from those which cumulatively do not substantially change the volume, hydrophobic-hydrophilic pattern and charge of the corresponding portion of the unsubstituted myasthenogenic peptide. Thus, a hydrophobic residue may be substituted with a hydrophilic residue, or vice-versa, as long as the total effect does not substantially change the volume, hydrophobic-hydrophilic pattern and charge of the corresponding unsubstituted myasthenogenic peptide. As indicated above, these substitutions are preferably made in the important epitopic core areas of residues 200–208 of SEQ ID NO:1 and 262–266 of SEQ ID NO:2.

It is preferred that the synthesized analog of the present invention have a length of at least nine amino acids and preferably from 9–12 amino acids. Each of the analogs preferably has from 1–3 substitutions in the core area.

In a preferred embodiment of the present invention, the substitution or substitutions are selected so as to substitute a hydrophobic amino acid residue in the core area with another hydrophobic amino acid residue selected so as not to cumulatively substantially change the volume of the unsubstituted peptide. For example, in p200-208, the hydrophobic amino acids are 201 Ile, 205 Phe, 206 Val and 207 Met. Each of these may be substituted with any of the other hydrophobic residues in this preferred embodiment. Thus, for example, 207 Met may be substituted with Gly,, Ala, Phe, Val, Leu, Ile, Pro or Trp. It has been established that substitution with Ala provides particularly flood results. Similarly, in p262-266, 263 Leu, 264 Ile and 265 Pro are all hydrophobic. Thus, from one to three of these can be substituted with another hydrophobic residue so long as the cumulative effect on the volume is not substantial. Thus, for example, the 265 Pro may be substituted by Gly, Ala, Phe, Val, Leu, Ile, Met or Trp.

In a second embodiment, a hydrophilic non-charged residue may be replaced by a charged or non-charged hydrophilic residue. Hydrophilic non-charged residues in the p200-208 peptide include 202 Thr, 203 Tyr and 208 Gln. In the p262-266 peptide, 266 Ser is a non-charged hydrophilic residue. Thus, for example, 208 Gln may be changed to any of Ser, Thr, Tyr, Arg, Lys, His, Asn, Asp or Glu and 266 Ser may be changed to any Thr, Gln, Tyr, Arg, Lys, His, Asn, Asp or Glu. Again, the change must be selected such that the cumulative effect of all changes does not substantially change the volume, hydrophobic-hydrophilic pattern and charge of the corresponding portion of the unsubstituted myasthenogenic peptide. Specific examples of changes within this embodiment are the substitution of 208 Gln with Asn or Asp and the substitution of 266 Ser with Lys or Asp.

In another embodiment of the present invention, charged hydrophilic residues are substituted by charged (same or opposite charge) or non-charged hydrophilic residues. In the p200-208 peptide, 200 Asp is a negatively-charged hydrophilic residue and 204 His is a positively-charged hydrophilic residue. In p262-266, 262 Glu is a negatively-charged hydrophilic residue. Thus, for example, 200 Asp may be substituted with Ser, Thr, Gln, Tyr, Arg, Lys, His, Asn or Glu and 262 Glu may be substituted with Ser, Thr, Gln, Tyr, Arg, Lys, His, Asn or Asp. Specific examples may be substituting 200 Asp with Lys (opposite charge) or 262 Glu with Ser (charged to non-charged). It has been found that substituting 262 Glu with Lys (negative charge to positive charge) gives particularly good results. Again, whatever substitution is made must be selected so as to not cumulatively substantially change the volume, hydrophobic-hydrophilic pattern and charge of the corresponding portion of the unsubstituted myasthenogenic peptide.

Finally, in a further embodiment, it, is also possible to replace a hydrophilic residue with a hydrophobic residue or vice-versa, as long as the cumulative effect is within the guidelines. Examples of such substitutions are the substitution of 204 His with Gly or 203 Tyr with Phe or the substitution of 262 Glu with Ala.

Those of ordinary skill in the art of peptide chemistry will readily recognize, by strictly theoretical considerations, what the cumulative effect will be on the charge, hydrophobic-hydrophilic pattern and volume of a given peptide as short as nine amino acids. Thus, it would not take undue experimentation to determine which substitutions should be tried in order to identify analogs in accordance with the present invention which have the function of competing with the native myasthenogenic peptides for binding the appropriate MHC Class II molecules but which will not lead to further activation of T cells.

It should be understood that the amino acids which are used for substituting into the native peptide may include modified peptides such as norleucine, hydrocyproline, hydroxylysine, gamma-carboxyglutamic acid, etc.

Some specific substitutions, any 1–3 of which which otherwise comply with the guidelines presented herein, may be present in an analog according to the present invention, include the following: 200, Asp-->Lys; 203, Tyr-->Phe; 204, His-->Gly; 207, Met-->NLeu; 207, Met-->Ala; 208, Gln-->Asp; 208, Gln-->Asn; 262, Glu-->Asp; 262, Glu-->Lys; 262, Glu-->Ser; 262, Glu--Ala; 265, Pro-->Leu; 265, Pro-->Phe; 266, Ser-->Lys; and 266, Ser-->Asp. The nomenclature of these analogs when including the entire p195-212 or p259-272 sequence except for one to three changes will hereinafter be by identification of the position and substituted residue only. The most preferred analogs are 204Gly, 207Ala, 262Lys, 262Ser, 265Leu and 265Phe, i.e., SEQ ID NOS: 5, 6, 11, 12, 14 and 15, respectively.

It is expected that the substitution of hydrophilic amino acids, that are mainly involved in T cell receptor interactions, will be effective in blocking T cell activation. Substitutions in the hydrophobic residues may contribute to higher stability of the analog-MHC complexes.

It should be understood that other modifications of the myasthenogenic peptides are also contemplated by the present invention. Thus, the peptide of the present invention is intended to include a "chemical derivative" thereof which retains at least a portion of the function of the peptide which permits its utility in preventing or inhibiting T cell proliferative responses and autoimmune disease.

A "chemical derivative" of a peptide of the present invention contains additional chemical moieties not normally a part of the peptide. Covalent modifications of the peptide are included within the scope of this invention. Such modifications may be introduced into the molecule by reacting targeted amino acid residues of the peptide with an organic derivatizing agent that is capable of reacting with selected side chains or terminal residues. Many such chemical derivatives and methods for making them are well known in the art.

Also included in the scope of the invention are salts of the peptides of the invention. As used herein, the term "salts" refers to both salts of carboxyl groups and to acid addition salts of amino groups of the peptide molecule. Salts of a carboxyl group may be formed by means known in the art and include inorganic salts, for example, sodium, calcium, ammonium, ferric or zinc salts, and the like, and salts with organic bases such as those formed for example, with amines, such as triethanolamine, arginine, or lysine, piperidine, procaine, and the like. Acid addition salts include, for example, salts with mineral acids such as, for example, hydrochloric acid or sulfuric acid, and salts with organic acids, such as, for example, acetic acid or oxalic acid. Such chemical derivations would preferably be used to modify the pharmaceutical properties of the peptide insofar as stability, solubility, etc., are concerned.

Once an analog in accordance with the present invention is produced, its ability to inhibit the proliferative response of T lymphocytes to the corresponding myasthenogenic peptides may be readily determined by those of ordinary skill in the art without undue experimentation using tests such as those described herein. One test which may be readily conducted is for the ability of substituted peptides to inhibit in vitro the proliferative responses of certain T cell lines and clones to the original peptide. The T cell lines and clones are those which have been produced which are specific to the myasthenogenic epitopes of SEQ ID NO:1 or SEQ ID NO:2. See Brocke et al. (1990a) and Kirshner et al. (1994), supra. Another test which can be conducted in order to select analogs having the desired activity is to test for the ability of the substituted peptides to inhibit the ability of the T cell lines and clones to provide help to peptide-specific B cells in the presence of the parent peptide. The substituted peptides may also be tested for their ability to bind directly, following biotinylation, to MHC Class II products on antigen-presenting cells of the relevant strains and to inhibit the binding of the parent myasthenogenic epitopes.

Substituted peptides which test positive in one or more of these in vitro tests will provide a reasonable expectation of in vivo activity. However, in vivo tests can also be conducted without undue experimentation. One such in vivo animal test would be to immunize naive mice with the myasthenogenic peptide and co-administer the mice with the analogs by various routes and dose schedules. Lymph node cells can then be analyzed for their proliferative potential to the myasthenogenic peptides. In addition, titers of anti-AChR antibodies in the sera of these mice can be measured to record the effect of the analogs on the in vivo helper cell activity. The advantages of these in vivo assays is that, although they are not aimed at assessing the effects of the analogs on disease induction, they allow in vivo screening of all analogs in a relatively short time.

As final proof of therapeutic activity, such activity may be directly measured in a murine model in vivo. It has previously been shown that some T cell lines and clones specific to the myasthenogenic T cell epitopes are capable of inducing MG-related autoimmune manifestations in mice (Mozes et al. (1991), "Abstracts", 15th International Congress of Biochemistry, Jerusalem, p.20 and Kirshner et al. (1994), supra). Therefore, naive mice can be injected with such clones and treated with the selected substitute peptides in order either to prevent or to remit the autoimmune responses. The peptides can be injected into the mice by different routes at different dosages and at different time schedules. In order to determine the pharmacokinetic parameters of the analogs, including volume of distribution, uptake into antigen-presenting cells and clearance, one can use biotinylated derivatives of the analogs. The concentration of the soluble fraction of the analogs in the various body fluids can be determined by ELISA, using avidin-coated plates and specific anti-peptide antibodies. Cell bound analogs can be analyzed by FACS, using fluorochrome-conjugated avidin or streptavidin. Furthermore, the treated mice can be tested periodically in order to determine the effect of the peptides on the autoimmune responses and on disease manifestations elicited in the mice by the T cell clones.

It can thus be seen that, besides the preferred embodiments which have been shown to be operable in the examples herein, those of ordinary skill in the art will be able to determine additional analogs which will also be operable following the guidelines presented herein without undue experimentation.

A relatively simple in vitro test can also be conducted in order to assay for the expected therapeutic efficacy of any given substituted peptide on any given myasthenia gravis patient. In order to assess the ultimate goal of producing peptides that will bind with high affinity to the appropriate MHC Class II molecules but will not lead to further activation of T cells and will therefore have a therapeutic effect on MG patients, the peptides may be assayed, following biotinylation, for their ability to bind directly to HLA Class II products on antigen-presenting cells in the peripheral blood lymphocytes of the myasthenia gravis patients and to inhibit the binding of the parent myasthenogenic epitopes. Healthy control donors and control peptides may be used in such assays to verify their specificity.

A preferred form of the therapeutic agent in accordance with the present invention is the form of a multi-epitope single peptide. Thus, in a preferred embodiment, analogs of each of the two myasthenogenic peptides are covalently linked to one another, such as by synthesizing them, either by chemical or biotechnological means, directly adjacent one another as a single peptide, or connecting them by means of a short stretch of alanine residues or by a putative site for proteolysis by cathepsin. See, for example, U.S. Pat. No. 5,126,249 and European Patent 495,049 with respect to such sites. This will induce site-specific proteolysis of the preferred form into the two desired analogs. The dual tandem analogs can have substantially the same activity as each of the analogs which are part of them and therefore have a therepeutic potential that will be capable of inhibiting T cell responses from a wide range of MG patients.

Alternatively, a number of the same or different substituted peptides of the present invention may be formed into a peptide polymer such as, for example, polymerization of the peptides with a suitable polymerization agent, such as 0.1% glutaraldehyde (Audibert et al. (1981), *Nature* 289:593). The polymer will preferably contain from 5 to 20 peptide residues. Such peptide polymers may also be formed by cross-linking the peptides or attaching multiple peptides to macromolecular carriers. Furthermore, the formulation may simply be a mixture of different peptides in accordance with the present invention.

Suitable macromolecular carriers are, for example, proteins, such as tetanus toxoid, and linear or branched copolymers of amino acids, such as a linear copolymer of L-alanine, L-glutamic acid and L-lysine and a branched copolymer of L-tyrosine, L-glutamic acid, L-alanine and L-lysine (T,G)-A-L, or multichain poly-DL-alanine (M. Sela (1969), *Science* 166: :1365–1374). The conjugates with the carriers are obtained, for example, by first coupling the peptide with a water-soluble carbodiimide, such as 1-ethyl-3 (3'-dimethylaminopropyl)carbodiimide hydrochloride, and then performing the conjugation with the macromolecular carrier as described by Langbeheim et al. (1976), *Proc. Natl. Acad. Sci. USA* 73:4636–4640. The contents of the coupled peptide in each conjugate are determined by amino acid analysis, in comparison to the composition of the carrier alone.

According to a preferred embodiment of the present invention, one or more active peptides may be attached to a suitable macromolecular carrier or may be polymerized in the presence of glutaraldehyde.

In a preferred embodiment of the present invention, the 207Ala and 262Lys were synthesized in tandem without chemical linkers or link sequences. Two peptides were synthesized, one in which the N-terminal sequence was that of 207Ala and the C-terminal sequence was that of 262Lys (designated 207Ala-262Lys (SEQ ID NO: 17)), and another in which the order of the analogs was reversed (designated 262Lys-207Ala (SEQ ID NO: 18)). Neither of the dual epitope analogs stimulated the proliferative responses of either the p195-212 or the p259-271 specific T cell lines. On the other hand, both dual analog peptides inhibited significantly the proliferative response of the latter lines to the myasthenogenic epitopes. Furthermore, both dual analogs were capable of inhibiting the in vivo priming of lymph node cells to either myasthenogenic epitope. It appeared that the dual analog 262Lys-207Ala was more efficient in inhibiting p195-212 specific responses than analog 207Ala-262Lys. No significant differences could be observed in the efficacy of inhibition of the p259-271 specific responses by the two dual analogs.

The inhibitory capacity of the two dual peptide analogs was tested on PBL of MG patients. The results demonstrated that the response to p195-212 of PBL of 21 out of 22 responder MG patients was inhibited by either dual analog. Similarly, PBL of 14 out of 16 MG patients that responded to p259-271 were inhibited by either 262Lys-207Ala or 207Ala-262Lys. Thus, both dual analogs appeared to be effective in inhibiting the responses of PBL of almost all MG patients tested to the myasthenogenic epitopes.

The peptides, polymers thereof or their conjugates with suitable macromolecular carriers, will be given to patients in a form that insures their bioavailability, making them suitable for treatment. If more than one peptide analog is found to have significant inhibitory activity, these analogs will be given to patients in a formulation containing a mixture of the peptides or as a single peptide in which both analogs are synthesized in tandem. If an individual patient responds to both pathogenic MG related peptides, namely p195-212 and p259-271, the ultimate treatment will contain the appropriate inhibitory analogs of both peptides in a suitable form.

The invention further includes pharmaceutical compositions comprising at least one synthetic peptide according to the invention, either single, tandem or multiple, a conjugate thereof with a suitable macromolecular carrier or a polymer thereof optionally with a pharmaceutically acceptable carrier.

The route of administration may include oral, intravenous, subcutaneous, intraarticular, intramuscular, by inhalation, intraperitoneal, intranasal, intrathecal, intradermal, transdermal or other known routes, including the enteral route. In vivo tests have established the efficacy of oral administration.

The dose ranges for the administration of the compositions of the present invention are those large enough to produce the desired effect, whereby, for example, an immune response to the myasthenogenic peptide, as measured by T cell proliferation in vitro, is substantially prevented or inhibited, and further, where the disease is significantly treated. The doses should not be so large as to cause adverse side effects, such as unwanted cross reactions, generalized immunosuppression, anaphylactic reactions and the like.

Effective doses of the peptides of this invention for use in treating an immune-related disease are in the range of about 1 $\mu$g to 100 mg/kg body weight. The dosage administered will be dependent upon the age, sex, health, and weight of the recipient, kind of concurrent treatment, if any, frequency of treatment, and the nature of the effect desired.

The synthetic analogs of sequences of the human AChR are aimed at inhibiting or suppressing specific antigen responses of MG patients, without harming other immune responses. This approach is of utmost importance since the currently accepted treatment for MG involves administration of immunosuppressive agents that are both non-specific and have multiple adverse side effects.

The invention will now be illustrated by the following non-limiting examples.

EXAMPLES

Example 1

Preparation of the Peptides

The synthetic peptides p195-212 and p259-271 and their analogs 200Lys; 203Phe; 204Gly; 207Ala; 208Asp; 208Asn; 209Lys; 262Asp; 262Lys; 262Ser; 265Ala; 265Leu; 265Phe; and 266Asp are synthesized by the Merrifield solid phase technique (Merrifield et al. (1963), *J. Am. Chem. Soc.* 85:2149), with a peptide synthesizer, using commercially available side-chain protected amino acids. Amino acids are added at each step with at least 99% efficiency. The protecting groups are removed and the peptides are cleared from the resin with anhydrous HF.

The peptides are purified by extraction with ethyl acetate or isopropyl acetate and by HPLC. The purity of the peptides is verified by HPLC and by amino acid analysis. The sequences and SEQ ID NOs of each of the above analogs are shown in FIGS. 8A and 8B.

While all of the above peptides have only one substitution each, other peptides having two or three substitutions and retaining the goals of the guidelines presented herein may be synthesized in the same manner.

Also synthesized in the same manner were two dual analogs, one in which the N-terminal sequence was that of 207Ala and the C-terminal sequence that of 262Lys (designated 207Ala-262Lys) and another in which the order of the analogs was reversed (designated 262Lys-207Ala). The sequences of these dual analogs and their SEQ ID NOs are shown in FIG. 8C.

Example 2
Inhibition of Proliferative Responses In vitro of T Cell Clones to Peptide p259-271

T cell lines and clones specific to p259-271 were developed from lymph node cells of high responder BALB/c mice according to the method described by Brocke et al. (1990a), supra, and designated TCBALB/c259-271 (Mozes, E. et al. (1991), supra; see also Kirshner et al. (1994), supra).

The proliferative response of the T cell clones was assessed by measuring $^3$H-thymidine incorporation into cells following incubation for the final 16 hours of culture. Cells ($10^4$ cells/well) of the T cell line TCBALB/c259-271 were incubated in the presence of irradiated (3000 rad) syngeneic spleen cells from BALB/c mice ($0.5\times10^6$ cells/well) as antigen-presenting cells, in the presence of various concentrations (1, 5, 10, 20 µg/well) of the peptides p195-212, p259-271, 266Asp, 262Lys and 262Asp. Cultures were set in 0.2 ml RPMI 1640 medium supplemented with 2 mM qlutamine, 1 mM sodium pyruvate, non-essential amino acids, 100 U/ml penicillin, 100 µg/ml streptomycin, 0.25 µg/ml fungizone, $5\times10^{-5}$ M 2-mercaptoethanol, 10 mM HEPES buffer (enriched medium) and 10% fetal calf serum (FCS), for 48 hr, followed by an overnight pulse with $^3$H-thymidine (0.5 µCi of 5 Ci/mmol). Following incorporation of the isotope, cells were harvested 16 hr later onto a filter paper and radioactivity was determined. The results are shown in FIG. 1 (expressed as mean CPM of triplicates ± SD). Peptides 266Asp and 262Asp triggered low proliferative responses of the T cell line at all doses tested (up to 12% and 34.3% respectively, of the response obtained with p259-271), whereas 262Lys did not stimulate the TCBALB/c259-271 cell line to proliferate.

Inhibition of the proliferative responses was performed by addition of increasing doses of the tested substituted peptides (25, 50, 75, 100 $\mu$g/well) into the in vitro proliferative cultures. Cells ($10^4$ cells/well) of the T cell line TCBALB/c259-271, were incubated in the presence of irradiated syngeneic spleen cells ($0.5\times10^6$ cells/well), p259-271 (1 $\mu$g/well) and the various doses of the inhibitory peptides 266Asp, 262Lsy and 262Asp and of p95-212, for 48 h. Thereafter, $^3$H-thymidine (0.5 $\mu$Ci of 5 Ci/mmol) was added, and 16 h later plates were harvested onto a filter paper. Results are expressed as % of inhibition of the p259-271 specific proliferative response. As shown in FIG. 2, 262Lys inhibited up to 93% of the proliferative response of the TCBALB/c259-271 line to p259-271. It is not surprising that peptide p195-212 is also shown to competitively inhibit proliferation of T cells specific for peptide p259-271, as p195-212 is directed to the same MHC-determinant as p259-271. Brocke et al. (1990a), supra, reports that p195-212 inhibits the proliferative response of the TCSW 259-271 T cell line and p259-271 inhibits the specific proliferative response of the TSSW 195-212 line.

Similar tests for the proliferative response of the other synthesized analogs were also conducted. The results with respect to all of these analogs are shown in Table 1. "Stimulators" are analogs that stimulated T cells; "inhibitors" are analogs that could not induce stimulation but could inhibit the stimulating activity of the myasthenogenic peptides; and "no effect" refers to analogs that neither stimulated nor inhibited T cells specific to the myasthenogenic peptides. At least for 203Phe analog of p195-212, direct binding measurements revealed its ability to bind to antigen-presenting cells of SJL strain mice, in which p195-212 is immunodominant.

TABLE 1

| Analog | Activity |
|---|---|
| Analogs of p195–212 | |
| 200 Lys | Stimulatory |
| 203 Phe | No effect |
| 204 Gly | Inhibitory |
| 207 Ala | Inhibitory |
| 208 Asp | Stimulatory |
| 208 Asn | Stimulatory |
| 209 Lys | Stimulatory |
| Analogs of p259–271 | |
| 262 Asp | No effect |
| 262 Lys | Inhibitory |
| 262 Ser | Inhibitory |
| 265 Ala | Stimulatory |
| 265 Leu | Inhibitory |
| 265 Phe | Inhibitory |
| 266 Asp | No effect |

Example 3

In vitro Antibody Production Assay

The synthetic peptides 266Asp, 262Lys and 262Asp were examined for their ability to stimulate the TCBALB/c259-271 T cell line to collaborate with peptide-specific B cells in an antibody production assay. B cells, purified from spleens of BALB/c mice previously immunized with 20 $\mu$g of p259-271, were cultured ($0.5\times10^6$ cells/well) with normal syngeneic spleen cells ($0.5\times10^6$ cells/well), different doses of 266Asp, 262Lys and 262Asp (0.001, 0.01, 0.1, 1 and 5 $\mu$g/well) and cells of the TCBALB/c259-271 line ($10^4$ cells/well), in 96-well microtiter plates. After 3 days incubation period, medium (enriched RPMI supplemented with 7.5% FCS) was exchanged with fresh medium without antigen, and 4 days later, supernatants were harvested and tested (by solid phase RIA) for the presence of specific anti-p259-271 antibodies. Results are expressed as mean CPM of triplicates ± SD.

As can be seen in FIG. 3, low antibody titers were obtained in the presence of 266Asp, whereas the helper activity stimulated by 262Asp was as efficient as that observed in the presence of the parent peptide. In contrast, no antibody activity could be detected when 262Lys was added to the culture.

Inhibition of the T cell helper activity was performed by addition of increasing doses of the tested substituted peptides into the in vitro culture mixtures. B cells, purified from spleens of BALB/c mice previously immunized with 20 $\mu$g of p259-271, were cultured ($0.5\times10^6$ cells/well) with normal syngeneic spleen cells ($0.5\times10^6$ cells/well), different doses of p259-271 alone (0.001, 0.01, 0.1, 1 and 5 $\mu$g/well) or together with 266Asp, 262Lys or 262Asp (20 $\mu$g of each) and cells of the TCBALB/c259-271 line ($10^4$ cells/well), in 96-well microtiter plates. After 3 days incubation period, medium as above was exchanged with fresh medium, and 4 days later, supernatants were harvested and tested (by solid phase RIA) for the presence of specific anti-p259-271 antibodies. Results are expressed as mean CPM of triplicates ± SD. As shown in FIG. 4, p259-271 specific antibody production was inhibited up to 80% in the presence of 262Lys.

Example 4
Antigen-specific Proliferative Response of Mouse Lymph Node Cells after Immunization with p259-271

In order to find out whether the peptides 266Asp, 262Lys and 262Asp will either stimulate or inhibit the proliferative response of a more heterogeneous T cell population, namely lymph nodes, the following experiments were performed.

The peptides 266Asp, 262Lys and 262Asp were examined for their ability to stimulate lymph node cells of p259-271 immunized BALB/c mice to proliferate, in comparison to the parent peptide p259-271. Lymph node cells ($0.5 \times 10^6$ cells/well) obtained from BALB/c mice immunized with p259-271, were incubated in enriched medium containing 1% normal mouse serum, in the presence of various concentrations of the peptides (10, 20, 50, 100 μg/well) for 96 h. Thereafter, $^3$H-thymidine (0.5 μCi of 5 Ci/mmol) was added and 16 h later plates were harvested onto a filter paper. Results are expressed as mean CPM of triplicates. As shown in FIG. 5, peptides 266Asp and 262Asp triggered low proliferative responses of the cells (up to 53.2% and 32.3% respectively, of that obtained by using p259-271) whereas 262Lys did not stimulate the lymph node cells to proliferate.

Figure 6:
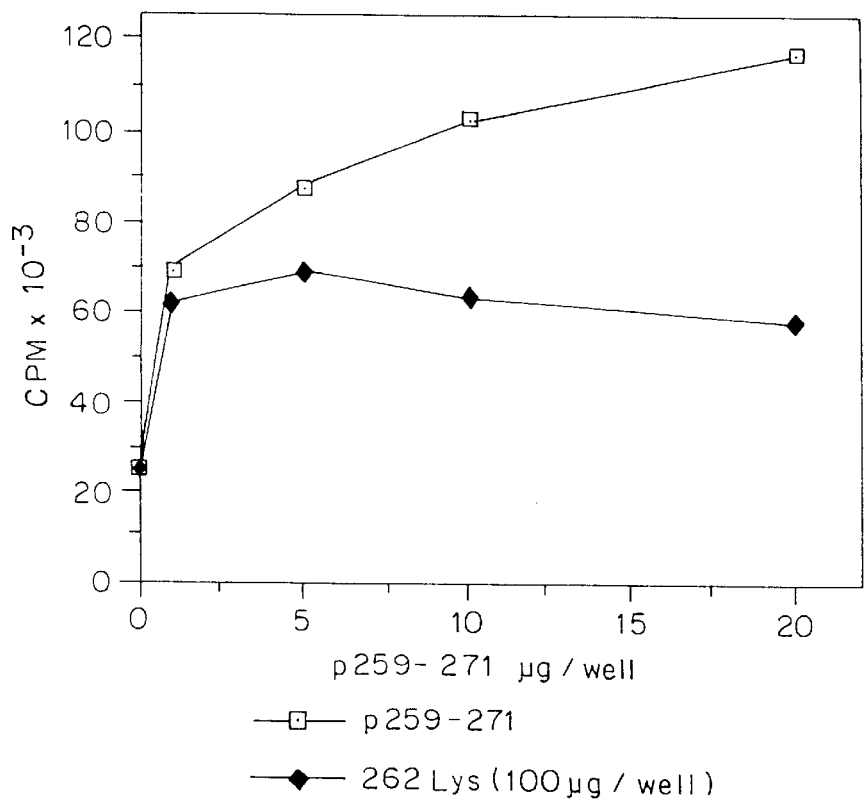
FIG. 6 is a graph showing inhibition of the proliferative responses of lymph node cells of BALB/c mice immunized with p259-271, to various doses of p259-271 alone or in combination with 262Lys.

Inhibition of the proliferative responses of lymph node cells of BALB/c mice immunized with p229-271 was done by adding the peptide analog 262Lys into the incubation mixture at the same time as the pathogenic peptide p259-271. Lymph node cells ($0.5 \times 10^6$ cells/well) obtained from BALB/c mice immunized with p259-271, were incubated in the presence of various concentrations of p259-271 (1, 5, 10, 20 μg/well) and 100 μg/well of 262Lys for 96 h. Thereafter, $^3$H-thymidine (0.5 μCi of 5 Ci/mmol) was added and 16 h later plates were harvested onto a filter paper. Results are expressed as mean CPM of triplicates. As shown in FIG. 6, the peptide 262Lys inhibited up to 64.7% of the proliferative response of the lymph node cells to p259-271.

Example 5
Inhibition of Proliferative Responses In vitro of T Cell Clones to Peptide p195-212

T cell lines and clones specific to p195-212 were established from lymph node cells of high (SJL) responder mouse strain by the method described by Brocke et al. (1990a), supra, and designated TCSJL195-212 line (Mozes, E. et al. (1991), supra; see also Kirshner et al. (1994), supra).

Figure 2:
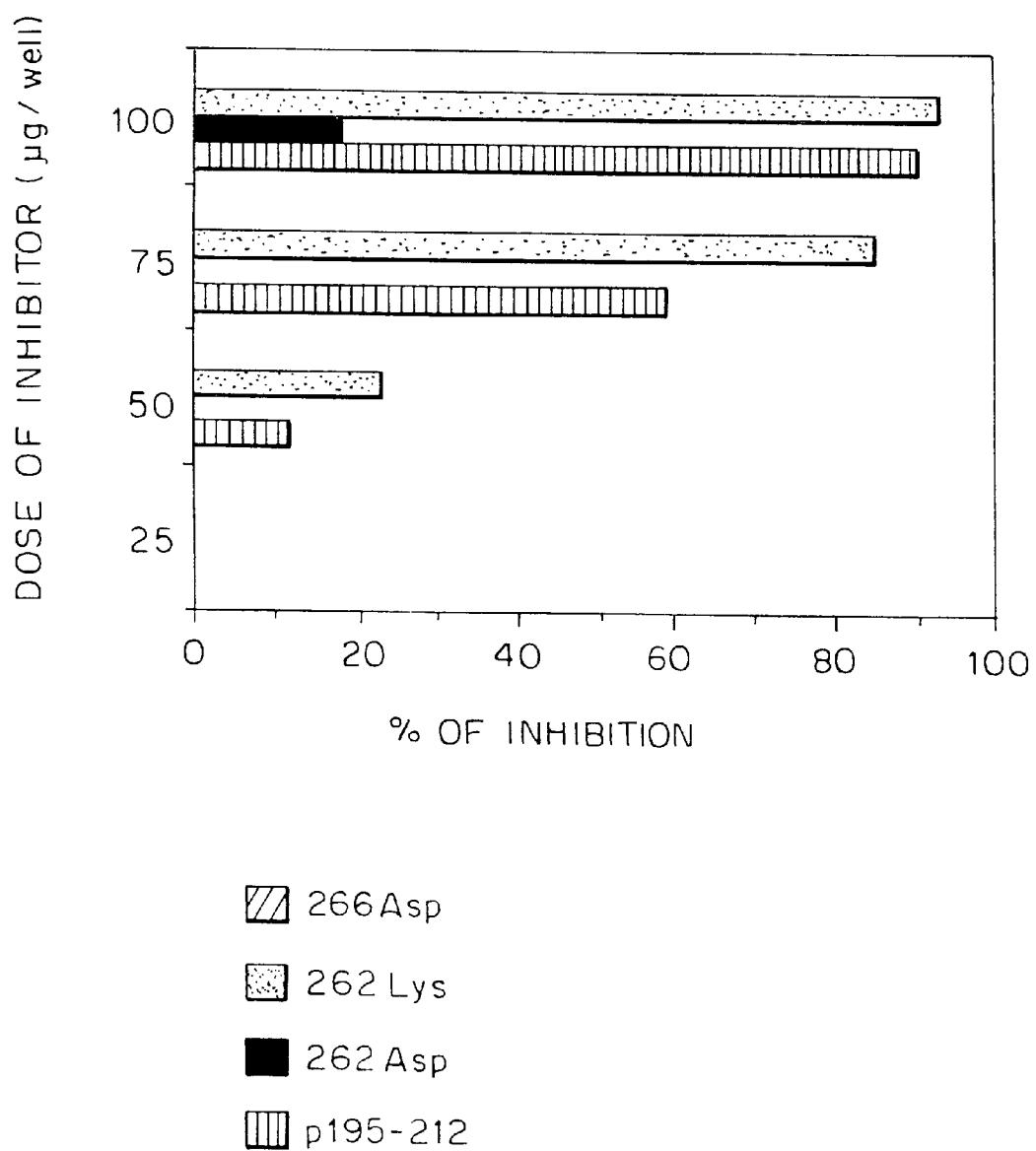
FIG. 2 is a graph showing inhibition of the p259-271 specific proliferative response of the T cell line TCBALB/c259-271, with various doses of the inhibitory peptides 266Asp, 262Lys, 262Asp and p195-212.
Figure 3:
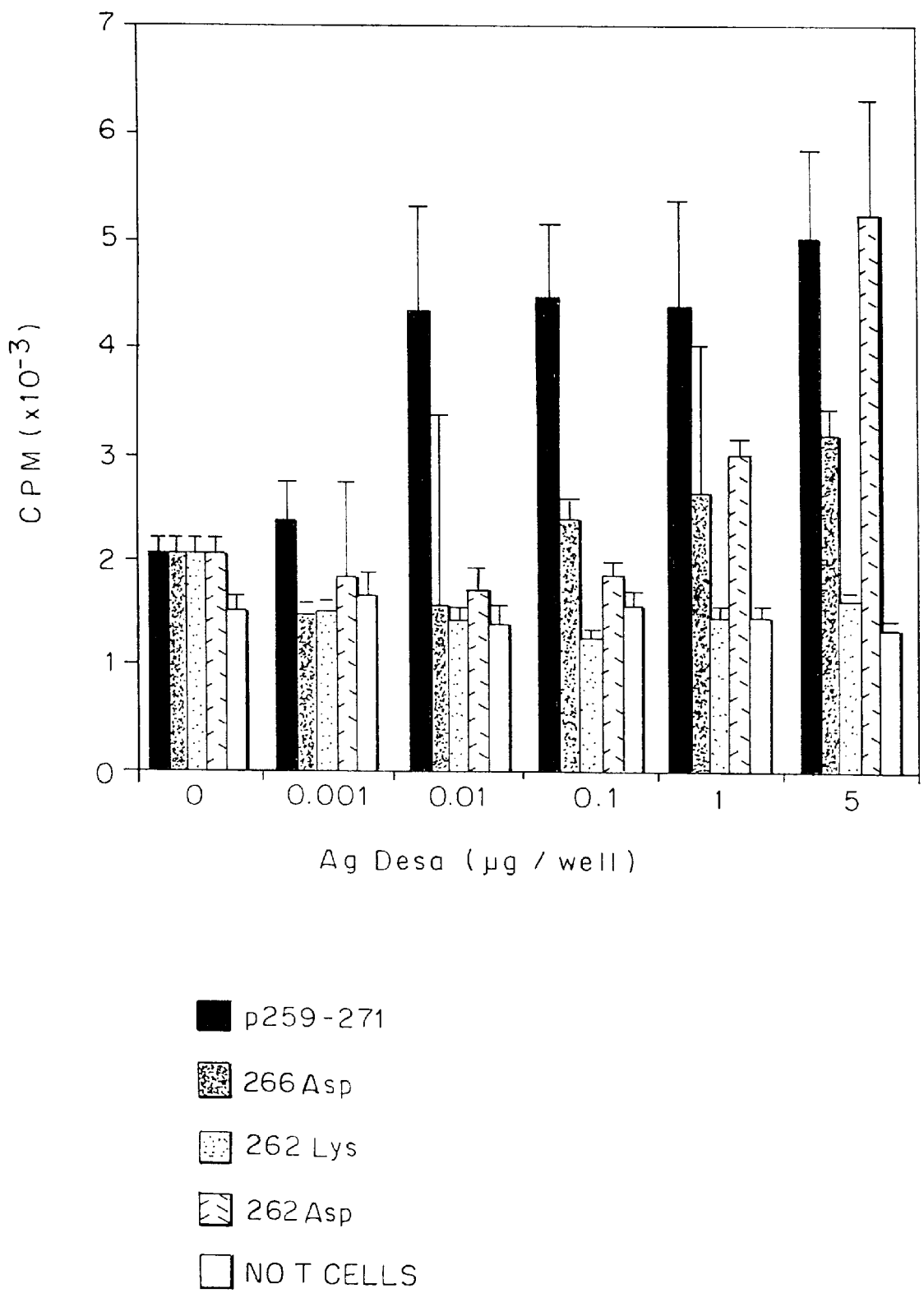
FIG. 3 is a graph showing specificity of the helper activity of the T cell line, TCBALB/c259-271, with various doses of the peptides (antigen=Ag) p259-271, 266Asp, 262Lys and 262Asp.

The proliferative response of the T cell clones was assessed as in the protocol Example 2 which resulted in FIG. 2.

Figure 7:
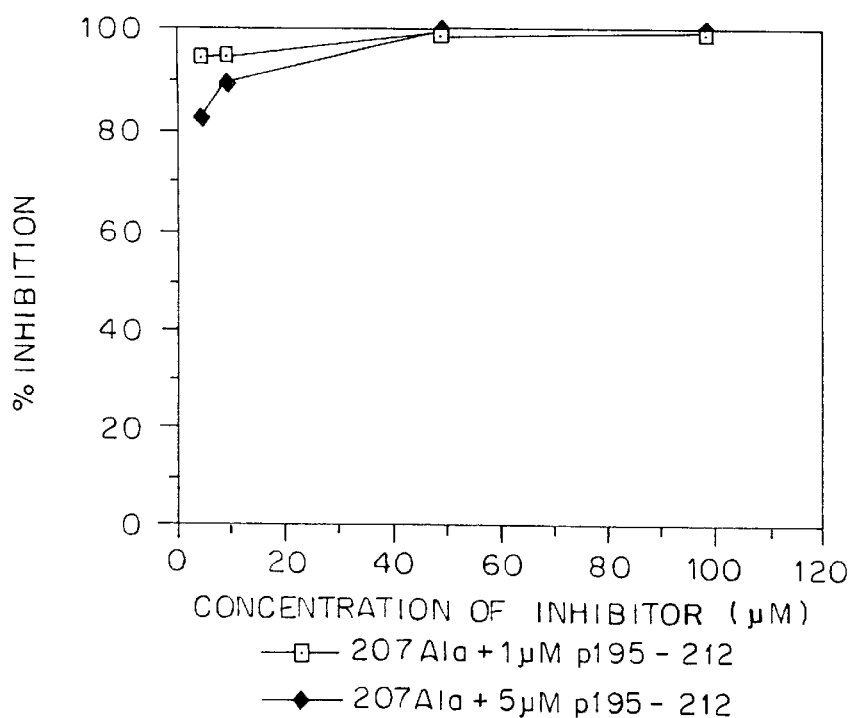
FIG. 7 is a graph showing inhibition of the p195-212 specific proliferative response of the T cell line, TCSJL195-212, with two different doses of mixtures of p195-212 with its analog 207Ala.

The p195-212 peptide analog, 207Ala, did not stimulate cells of the TCSJL195-212 line to proliferate. Moreover, as shown in FIG. 7, 207Ala inhibited more than 99% of the proliferative response of the TCSJL195-212 line to p195-212. This represents very substantial inhibition.

Example 6
Inhibition of Proliferation of Human T Cells to the Pathogenic Peptides of Myasthenia Gravis The action of the pathogenic peptide p259-271 and its analogs 266Asp, 262Lys and 262Asp, and of p195-212 and its analog 207Ala, on proliferative responses of human T cells was assessed.

Peripheral blood lymphocytes (PBL) of myasthenia gravis patients and of the appropriate control donors ($2 \times 10^5$ cells/well) were assayed in microtiter plates in 0.2 ml enriched medium containing 10% autologous serum, in the presence of different doses of the peptides p195-212 and the analog 207Ala for 96 h, followed by an overnight pulse with 0.5 μCi of $^3$H-thymidine. Cells were harvested and radioactivity determined. Inhibition of the proliferative responses was done by adding different doses of 207Ala into the incubation mixture at the same time as the pathogenic peptide p195-212. Results are reported in Table 2 as (SI) stimulation indices (col. 2 and 3), % inhibition (col. 4).

The PBL of MG patients were tested for their ability to proliferate in the presence of p195-212 and the peptide analog 207Ala. Further, the ability of the analog 207Ala to inhibit p195-212 specific proliferative responses of the PBL was tested. Table 2 summarizes the responses of three MG patients in these tests. As can be seen in this table, PBL from patients E.K., C.G. and M.R. proliferated in response to p195-212 (SI=6.3, 4.3 and 3.6, respectively), whereas no proliferative responses to the analog were detected at all concentrations (10, 25, 50, 100 μM, corresponding to 20, 50, 100, 200 μg/well) tested. In addition, the analog was able to inhibit the proliferative responses of the PBL from all three patients by 77–100% at an Inhibitor:Stimulator (I:S) ratio of 1:1.

TABLE 2

Peripheral Blood Lymphocyte Proliferative Responses of Myasthenia Gravis Patients to p195–212 and its Analog 207 Ala

| Patient | p195–212 SI* (μg/well) † | Analog SI (μg/well) | % Inhibition (207 Ala:p195–212) |
|---|---|---|---|
| E.K. | 6.3 (50) | 1 | 77 (1:1) |
| C.G. | 4.3 (25) | 1 | 100 (1:1) |
| M.R. | 3.6 (25) | 1 | 100 (1:1) |

*Stimulation Index = response/background
† Concentration of peptide at SI

The PBL of MG patients were assayed as above for their ability to proliferate in the presence of different doses of p259-271 and its analogs 266Asp, 262Lys and 262Asp. In addition, the ability of different doses of the analogs to inhibit p259-271 specific proliferative responses of the PBL was tested. Table 3 summarizes the responses of three MG patients in these tests. As can be seen in this table, PBL from patients I.T., E.K. and C.G. proliferated in response to p259-271 (SI=4.1, 3.7 and 2.7, respectively). Moreover, for each patient, at least one analog was able to inhibit the p259-271 induced proliferative response of the PBL.

TABLE 3

Peripheral Blood Lymphocyte Response of Myasthenia Gravis Patients to p259–271 and its Analogs

| Patient | p259–271 SI* (μg/well) † | 266 Asp % Inhibition (I:S) ** | 262 Lys % Inhibition (I:S) | 262 Asp % Inhibition (I:S) |
|---|---|---|---|---|
| I.T. | 4.1 (25) | 34.3 (4:1) | 0 | 78 (1:1) |
| E.K. | 3.7 (100) | 82.7 (1:1) | 100 (1:1) | 70 (1:1) |
| C.G. | 2.7 (100) | 85.6 (1:1) | 71.6 (1:1) | 65 (1:1) |

*Stimulation Index = response/background
† Concentration of peptide at SI
** Inhibitory peptide:Stimulating peptide A larger experiment on 40 MG patients has also been conducted using analogs 207Ala, 204Gly, 262Lys and 262Ser. Out of 40 MG patients that were tested for this purpose 25 (63%) responded to p195-212 and 23 (580%) responded to p259-271. Seventy eight percent of the patients responded to either or both myasthenogenic peptides. Analog 207Ala inhibited the response of PBL of 23 out of 24 (96%) responder MG patients and peptide analog 204Gly inhibited the responses of PBL of 24 (100%) MG patients to p195-212. Similarly, the responses to p259-271 of PBL of 19 and 18 MG patients out of 20 tested were inhibited by analogs 262Lys and 262Ser, respectively. Thus, the peptide analogs are very efficient in inhibiting the responses of PBL of almost all responder MG patients to the myasthenogenic epitopes.

The inhibitory capacity of the two dual peptide analogs was also tested on PBL of MG patients. The results demonstrated that the response to p195-212 of PBL of 21 out of 22 responder MG patients was inhibited by either dual analog. Similarly, PBL of 14 out of 16 MG patients that responded to p259-271 were inhibited by either 262Lys-207Ala or 207Ala-262Lys. Thus, both dual analogs appeared to be effective in inhibiting the responses of PBL of almost all MG patients tested to the myasthenogenic epitopes. The results of these tests are shown in Tables 4 and 5.

TABLE 4

Inhibitory Capacity of p195–212 Based Analogs on Stimulation of PBL of MG Patients in the Presence of p195–212

| Analog | Inhibitory activity | % Inhibition Mean ± SD | Range |
|---|---|---|---|
| 204 Gly | 100% (24/24) | 83.2 ± 22.5 | 23–100 |
| 207 Ala | 96% (23/24) | 80.5 ± 21.9 | 35–100 |
| 207 Ala–262 Lys | 95% (21/22) | 89.9 ± 18.9 | 40–100 |
| 262 Lys–207 Ala | 95% (21/22) | 97.6 ± 5.7 | 79–100 |

TABLE 5

Inhibitory Capacity of p259–271 Based Analogs on Stimulation of PBL of MG Patients in the Presence of p259–271

| Analog | Inhibitory activity | % Inhibition Mean ± SD | Range |
|---|---|---|---|
| 262 Lys | 95% (19/20) | 91.8 ± 15.8 | 39–100 |
| 262 Ser | 90% (18/20) | 88.2 ± 14.9 | 57–100 |
| 207 Ala–262 Lys | 94% (16/17) | 84.6 ± 21.3 | 36–100 |
| 262 Lys–207 Ala | 88% (15/17) | 90.1 ± 21.4 | 23–100 |

Example 7
Induction and Treatment of Experimental MG in Mice

As described above (Mozes (1991) and Kirshner (1994)), both p195-212 specific T cell line of SJL origin and p259-271 T cell line of BALB/c origin, are capable of initiating MG-related manifestations upon inoculation into naive syngeneic mice. Such MG-related manifestations have been demonstrated by the production of autoantibodies to self (murine) AChR and by the determination of compound muscle action potential (CMAP) decrement. This is accomplished by inoculating naive syngeneic mice (i.v. in PBS 1 to 4 times) with activated peptide specific T cells of the lines TCSJL195-212 and TCBALB/c259-271 or their derived clones (5–10×10$^6$ cells).

Figure 9:
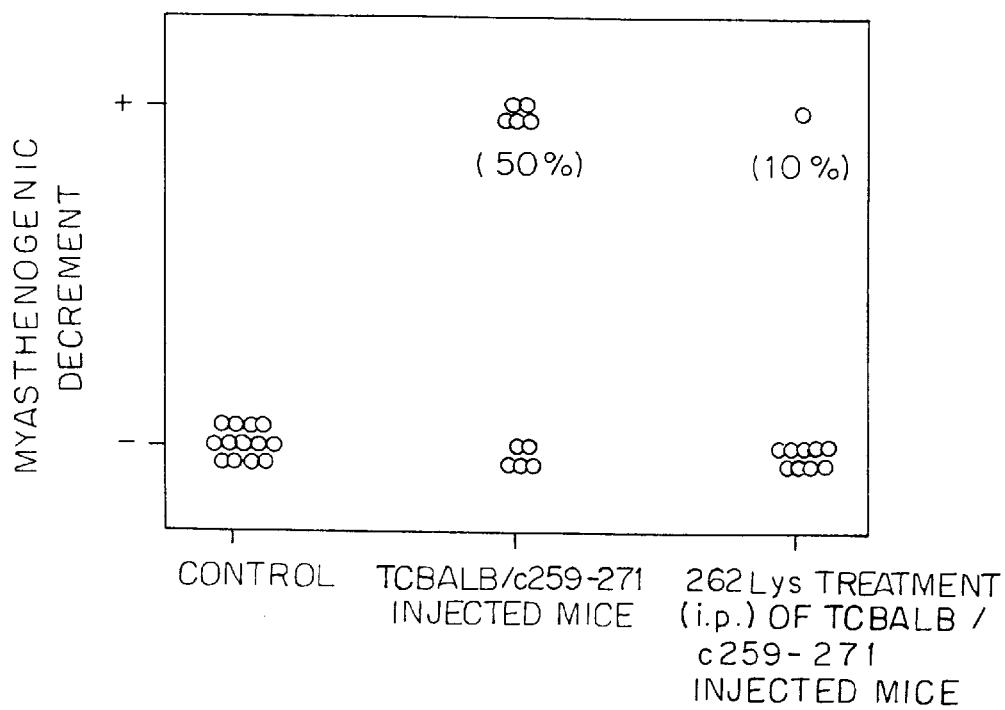
FIG. 9 is a graph showing the results of an experiment showing the prevention of experimental autoimmune myasthenia gravis (EAMG) induction by an analog of the present invention. The plus sign (+) opposite "myasthenogenic decrement" indicates that a CMAP decrement was determined. The negative sign (−) indicates that no CMAP decrement was found.

To find out whether the peptide analogs are capable of inhibiting the induction of experimental MG, a first group of 10 BALB/c mice was injected with cells of the p259-271 specific line while a second group of 10 BALB/c mice was injected with the T cell line concomitant with 200 μg of analog 262Lys. Whereas in 5 of the 10 mice injected with the T cell line CMAP decrements could be determined, in only 1 of the 10 mice that were treated with the peptide analog could a CMAP decrement be detected. In none of the 13 control mice CMAP decrements could be determined. Thus, analog 262Lys is capable of inhibiting the clinical manifestations of experimental MG. The results of this experiment are graphed in FIG. 9.

Example 8
Binding of Analogs to MHC

Since the aim of the present invention is to design peptide analogs that will bind efficiently to MHC class II on antigen presenting cells but will not stimulate the specific T cells for proliferation, the binding capacity of the peptide analogs was compared to that of the myasthenogenic peptides. The binding of the biotinylated peptide analogs 207Ala, 204Gly, 207Ala-262Lys and 262Lys-207Ala to MHC class II on murine and human antigen presenting cells has been analysed.

Biotinylation of Peptide

N-Terminal biotinylation of peptide p195-212 and its derived analogs, including the dual analog 207Ala-262Lys, was performed in 0.1N sodium bicarbonate solution at 0° C. with a two fold molar excess of biotin-N-hydroxysuccinimide (Sigma Chemical Co., St. Louis, Mo.) dissolved in dimethylsulfoxide (5 mg/ml). N-terminal biotinylation of p259-271and its derived analogs, including the dual analog 262Lys-207Ala, was performed in 0.1N sodium bicarbonate solution at room temperature, with a two fold molar excess of biotinamidocaproate N-hydroxysuccinimide ester (Sigma) dissolved in 1-methyl-2-pyrrolidone (5 mg/ml). The addition of a caproyl spacer between the biotin moiety and Val$^{259}$ of p259-271-based peptides was necessary to allow the detection of MHC-peptide interactions by streptavidin (Zisman et al., *Internat. Immunol.*, 6:683 (1.994)).

Direct Binding of Biotinylated Peptides to APC of Human Subjects

APC of patients with the autoimmune disease MG and of healthy donors were collected from the Ficoll fraction following Ficoll-Hypaque density centrifugation (Pharmacia Fine Chemicals, Uppsala, Sweden). The cells in this fraction were mainly monocytes and granulocytes with less than 10% lymphocytes, as determined by direct staining with FITC conjugated- anti-CD14, anti-CD3 and anti-B220 (Sigma), and were used as APC in the binding experiments. Alternatively, PBL were isolated from the whole blood by Ficoll-Hypaque density centrifugation, washed, suspended in 10% fetal calf serum (FCS) in RPMI 1640, and incubated in Petri dishes (5×10$^7$ cells/5 ml/dish, Nunc, Roskilde, Denmark) at 37° C. for 1 hr. Thereafter non-adherent cells were removed and the plates were washed three times with RPMI and placed on ice. Adherent cells were collected using a rubber policeman, and were used as APC in the binding experiments. The cells in this fraction also contained less than 10% lymphocytes, as determined by direct staining with FITC conjugated- anti-CD14, anti-CD3 and anti-B220.

The APC were washed twice with a solution of phosphate buffered saline (PBS, pH=7.4) containing 0.1% bovine serum albumin (BSA, high purity grade, Amresco, Ohio, further referred to as PBS/BSA), and were incubated (1×10$^6$/sample) for 20 hr with the biotinylated peptides or with PBS/BSA alone, in a 37° C. incubator containing 5% $CO_2$, followed by incuation with phycoerythrin (PE)-conjugated streptavidin (1:40, Jackson Immunoresearch, West Grove, Pa.) at 4° C. for 30 min as described for murine splenic adherent cells (Zisman et al. (1994) supra; Mozes et al., *EMBO J.*, 8:4049 (1989)). After each incubation the cells were washed twice at 40° C. with the above solution.

To amplify the fluorescence signal an extended staining procedure was used. In this protocol, the incubation with PE-streptavidin was followed by incubations with biotinylated anti-streptavidin (1:60, Vector Laboratories, Burlingame, Calif., USA) and a second incubation with PE-streptavidin, both at 4° C. for 30 min.

Thereafter, the cells were analyzed by flow cytometry using the FACScan cytometer and lysis software or the FACSort cytometer and CELLQuest software (Becton-Dickinson, Mountain View, Calif., USA). In each analysis minimally 5,000 cells were examined. Dead cells were excluded on the basis of the forward- and side-angle light scatter. Binding data were presented as MFI, mean fluorescence intensity of the cells in the presence or absence of the biotinylated peptide. Alternatively, percentage of bound cells was calculated and presented as net values above the background signal of cells that were incubated in the absence of biotinylated peptides.

In a similar manner binding of the biotinylated peptide to MHC class II of SJL mice was determined.

Results

For both species, the binding of analog 207Ala to MHC class II was better than that of analog 204Gly and at least as good as that of the myasthenogenic epitope p195-212. The affinity of the binding of the dual analog 262Lys-207Ala to MHC class II of SJL mice has been calculated to be 10-fold higher than that of its counterpart dual analog 207Ala-262Lys. Furthermore, the pattern of the binding of the dual analog 262Lys-207Lys is more homogeneous than that of the myasthenogenic peptide p195-212. These results indicate that the dual epitope analogs are of therapeutic value.

Example 9
Inhibition of Proliferative Responses by the Dual Epitope Analogs

Figure 10:
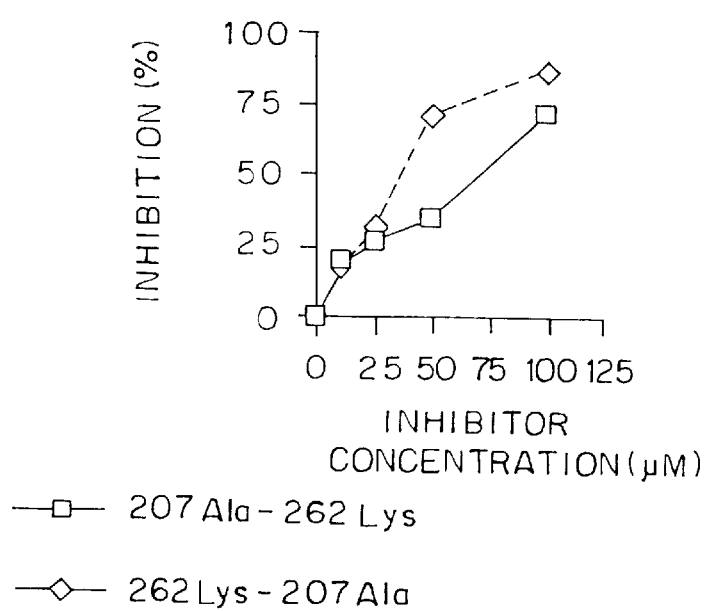
FIG. 10 is a graph showing the inhibition of proliferative responses of T cell line TCSJL195-212 by the dual epitope analogs 207Ala-262Lys and 262Lys-207Ala.
Figure 11:
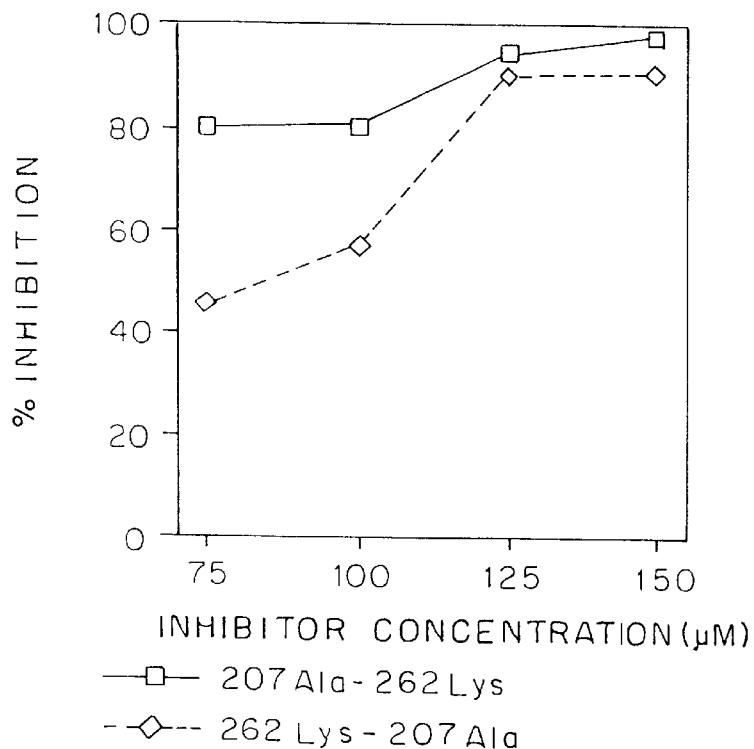
FIG. 11 is a graph showing the inhibition of proliferative responses of T cell line TCBALB/c259-271 by the dual epitope analogs 207Ala-262Lys and 262Lys-207Ala.
Figure 12:
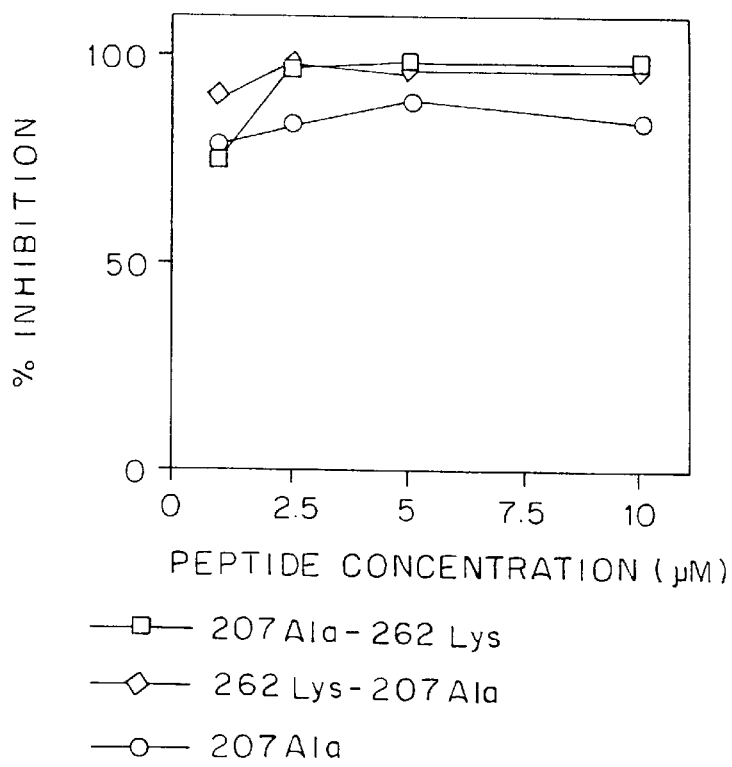
FIG. 12 is a graph showing the in vivo inhibition of the priming of lymph node cells by the p195-212 based analogs 207Ala, 207Ala-262Lys and 262Lys-207Ala.
Figure 13:
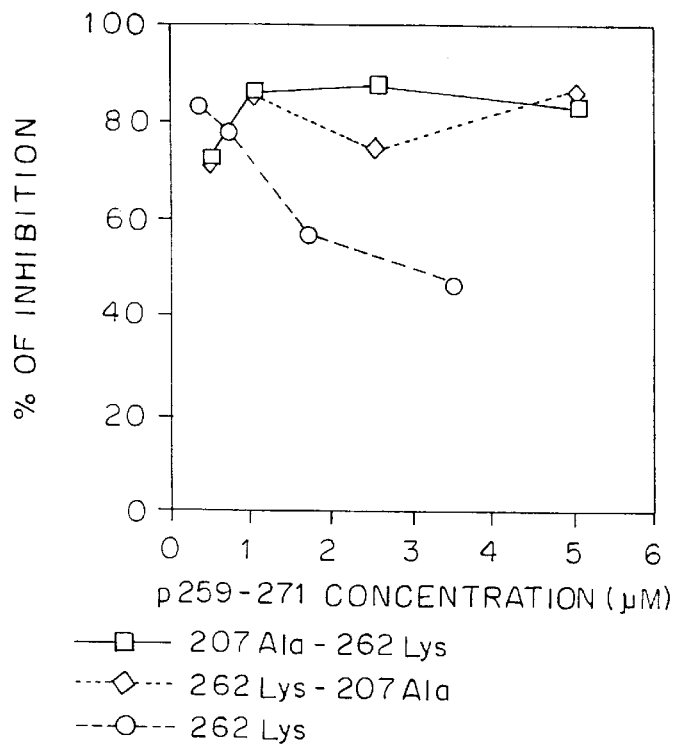
FIG. 13 is a graph showing the in vivo inhibition of the priming of lymph node cells by the p259-271 based analogs 262Lys, 207Ala-262Lys and 262Lys-207Ala.
Figure 14:
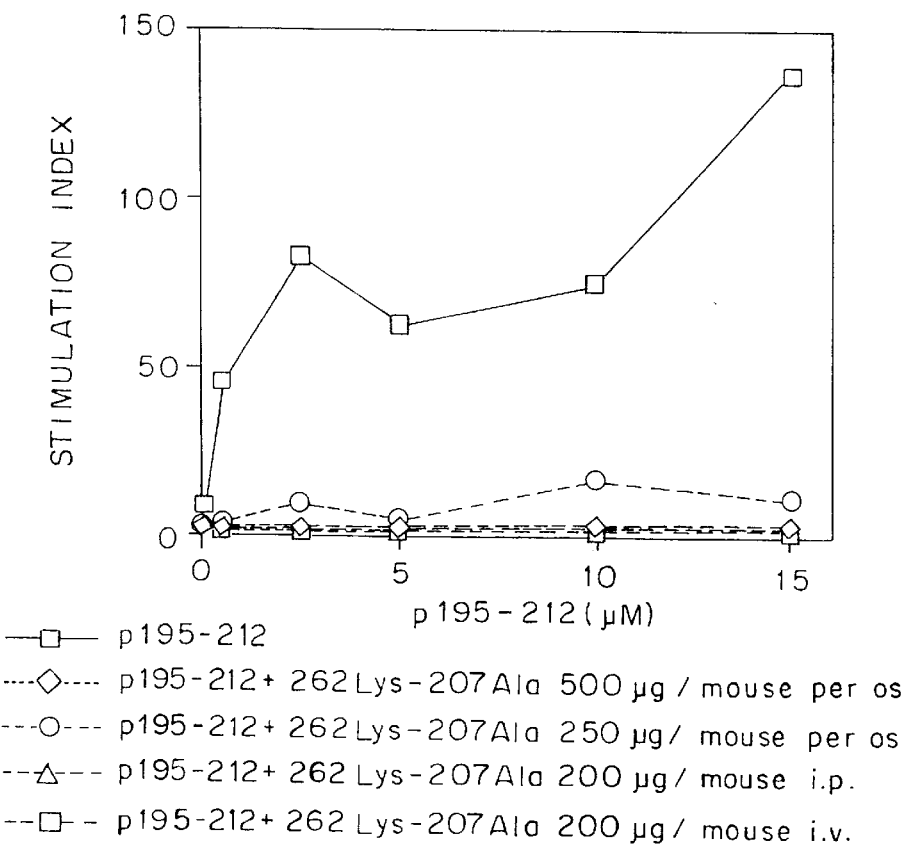
FIG. 14 is a graph showing the inhibition of lymph node cell proliferation of p195-212 immunized SJL mice by per os administration of 262Lys-207Ala.
Figure 15:
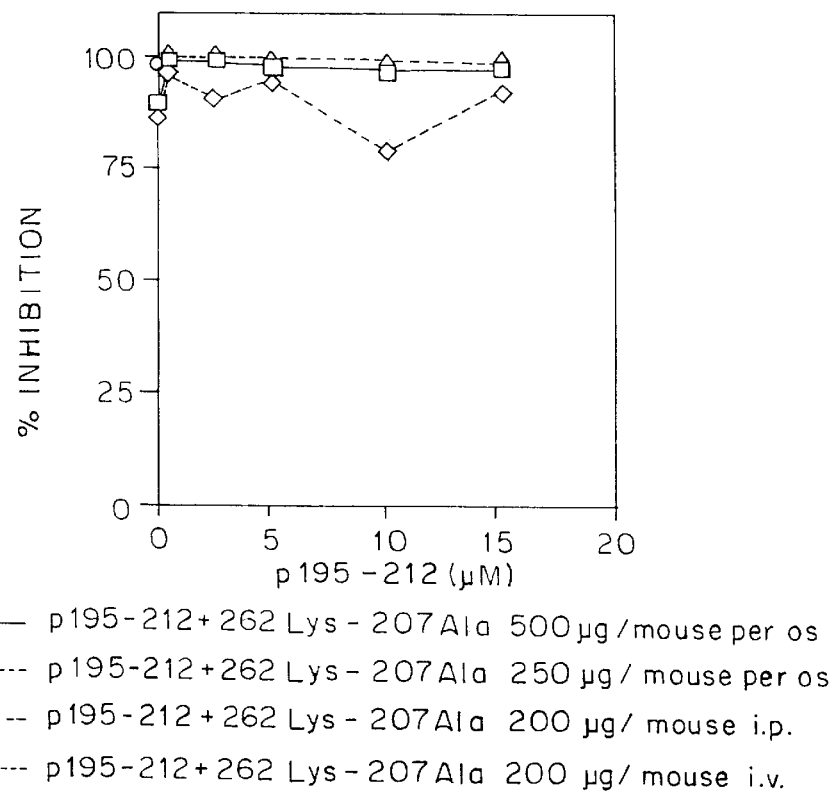
FIG. 15 is a graph showing the percent inhibition of lymph node cell proliferation of p195-212 immunized SJL mice by per os administration of 262Lys-207Ala.
Figure 16:
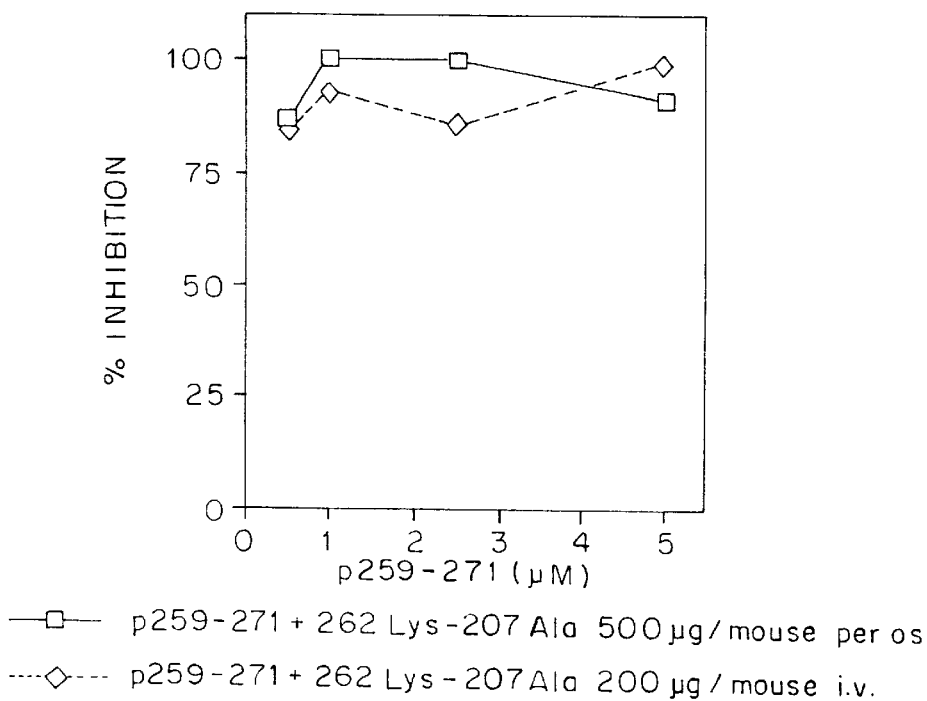
FIG. 16 is a graph showing the percent inhibition of lymph node cell proliferation of p259-271 immunized BALB/c mice by per os administration of 262Lys-207Ala.

Cells ($10^4$ per well) of the T cell Line TCSJL195-212 or TCBALB/c259-271 were incubated in the presence of irradiated syngeneic spleen cells ($0.5 \times 10^6$), either p195-212 or p259-271 (10 $\mu$M) and various concentrations of the dual epitope analogs 207Ala-262Lys or 262Lys-207Ala for 48 h. Thereafter, $^3$H-thymidine was added and 16 h later plates we harvested. The results, expressed as % inhibition of the p195-212 or p259-271 specific proliferative response, are shown in FIGS. 10 and 11.

Inhibition of the non-specific proliferative response of the TCBALB/c259-271 line to Con-A sup was also tested. 207Ala-262Lys inhibited this proliferative response up to 67.8% at a concentration of 100 mM or up to 73% at 150 mM. 262Lys-207Ala did not inhibit this proliferation non-specifically. These results indicate that the dual analog 262Lys-207Ala inhibits the proliferative responses of both the TCSJL195-212 and TCBALB/c259-271 T cell lines very efficiently and specifically.

Example 10

In vivo Inhibition of Priming of Lymph Node Cells

SJL mice were injected intradermally in the hind footpads with 10 $\mu$g of p199-212 (100 $\mu$l) in CFA, concomitant with intravenous inoculation of a competitor peptide in PBS (500 $\mu$l). The competitor peptides were 207Ala, 207Ala-262Lys and 262Lys-207Ala. Lymph node cells obtained from the mice were incubated in the presence of various concentrations of p199-212 for 96 h. Thereafter $^3$H-thymidine was added and 16 h later cells were harvested and radioactivity was counted. Results, expressed as percent inhibition of the p199-212 specific proliferative response, are shown in FIG. 12.

BALB/c mice were injected intradermally in the hind footpads with 10 $\mu$g of p259-271 in CFA (100 $\mu$l) concomitant with an i.v. inoculation of the analogs 262Lys, 207Ala-262Lys or 262Lys-207Ala, (200 $\mu$g) in 500 $\mu$l of PBS. Lymph node cells obtained from the mice were incubated in the presence of various concentrations of p259-271 for 96 h. Thereafter $^3$H-thymidine was added and 16 h later cells were harvested and radioactivity was counted. Results, expressed as percent of inhibition of the p259-271 specific proliferative response, are shown in FIG. 13.

Example 11

Inhibition of Lymph Node Cell Proliferation by Oral Feeding with the Dual Analog In order to assess the efficacy of the dual analog 262Lys-207Ala in inhibiting T cell proliferative responses to the myasthenogenic T cell epitopes, namely p195-212 and p259-271, the following experiments were performed:

1) SJL mice were injected intradermally in the hind footpads with 10 $\mu$g of p195-212 in CFA (100 $\mu$l) concomitant with an either i.v. or i.p. inoculation of the dual analog 262Lys-207Ala (200 $\mu$g) in 500 $\mu$l of PBS. Two additional groups were fed with either 205 $\mu$g/mouse or 500 $\mu$g/mouse of the dual analog in 300 $\mu$l of PBS. Ten days later the mice were sacrificed and their lymph node cells were incubated in the presence of different concentrations of p195-212 for 96 hours. Thereafter $^3$H-thymidine was added and 16 hours later cells were harvested and radioactivity was counted. FIG. 14 represents the stimulation indices obtained in the proliferation assay of the lymph node cells in the different groups. As can be seen, the efficient proliferation obtained in the group that was only immunized with p195-212 was completely inhibited in the groups that were either injected with 200 $\mu$g of the dual analog in PBS i.v. or i.p. or fed with 500 $\mu$g of the analog. A dramatic inhibition was observed in the group of mice that was fed with 250 $\mu$l as well.

FIG. 15 shows the percentage of inhibition obtained in the latter experiment. As can be seen, oral administration of 500 $\mu$g of the dual analog completely inhibited the proliferation of lymph node cells to the myasthenogenic T-cell epitope, p195-212.

2) FIG. 16 demonstrates the results of an experiment in which BALB/c mice were immunized with the second myasthenogenic peptide, namely p259-271 in CFA (20 $\mu$g/mouse) and were either injected with the dual analog 226Lys-207Ala i.v. (200 $\mu$g/mouse in PBS) or fed with 500 $\mu$g/mouse in PBS. Results are expressed in the Figure as percentages of inhibition of the proliferative responses in the presence of different concentrations of the myasthenogenic epitopes, p259-271. As can be seen, the per os route of administration of the dual analog is at least as effective in inhibiting the proliferative response as the i.v. injection.

In order to prevent or cure the induced experimental MG, peptide analogs may be administered a) before inoculation of the peptide specific T cells; b) concomitant with inoculation of the peptide specific T cells; c) after inoculation with the peptide specific T cells but before the appearance of autoimmune responses; or d) after the appearance of experimental MG. Reduction in the severity of the autoimmune response indicates suitability of treatment with the peptide.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional method steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary is skill in the art.

We claim:

1. A response-inhibiting peptide of at least nine amino acid residues capable of inhibiting the proliferative response of T lymphocytes from a myasthenia gravis patient to a myasthenogenic peptide corresponding to a sequence of the human acetylcholine receptor α-subunit selected from the group consisting of peptide p195-212 having the formula of SEQ ID NO:1:

```
     195              200              205
    Asp-Thr-Pro-Tyr-Leu-Asp-Ile-Thr-Tyr-His-Phe-
                    210
    Val-Met-Gln-Arg-Leu-Pro-Leu
``` and the peptide p259-271 having the formula of SEQ ID NO:2:

```
     260              265              270
    Val-Ile-Val-Glu-Leu-Ile-Pro-Ser-Thr-Ser-Ser-Ala-Val
``` said response-inhibiting peptide comprising an amino acid includes at least amino acid residues 200–208 of SEQ ID NO:1 or amino acid residues 262–266 of SEQ ID NO:2, but differing therefrom by one to three amino acid substitutions, said substitutions being selected so as to have the function of inhibiting the proliferative response of T lymphocytes from a myasthenia gravis patient to the myasthenogenic peptide SEQ ID NO:1 or SEQ ID NO:2 to which it corresponds, said substitutions being selected from the group consisting of:

201 Ile, 205 Phe, 206 Val, 207 Met, 263 Leu, 264 Ile and 265 Pro being substituted by a different one of any of the amino acids Met, Gly, Ala, Phe, Val, Leu, Ile, Pro or Trp;

200 Asp, 202 Thr, 203 Tyr, 204 His, 2:08 Gln, 262 Glu, and 266 Ser being substituted by a different one of any of the amino acids Glu, Ser, Thr, Tyr, Arg, Lys, His, Asn, Asp or Glu;

204 His being substituted with Gly;

203 Tyr being substituted with Phe;

207 Met being substituted with NLeu; and

262 Glu being substituted with Ala.

2. A response-inhibiting peptide according to claim 1, wherein said myasthenogenic peptide is p195-212 and said amino acid substitutions are selected so as to have the function of inhibiting the proliferative response of T lymphocytes from a myasthenia gravis patient to said myasthenogenic peptide p195-212.

3. A response-inhibiting peptide according to claim 2, wherein the methionine (Met) residue at position 207 is replaced by an alanine residue (Ala).

4. A response-inhibiting peptide according to claim 1, wherein said myasthenogenic peptide is p259-271 and said amino acid substitutions are selected so as to have the function of inhibiting the proliferative response of T lymphocytes from a myasthenia gravis patient to said myasthenogenic peptide p259-271.

5. A response-inhibiting peptide according to claim 4, wherein the serine (Ser) residue at position 266 is replaced by an aspartic acid residue (Asp).

6. A response-inhibiting peptide according to claim 4, wherein the glutamic acid residue (Glu) at position 262 is replaced by a lysine residue (Lys).

7. A response-inhibiting peptide according to claim 4, wherein the glutamic acid residue (Glu) at position 262 is replaced by an aspartic acid residue (Asp).

8. A response-inhibiting peptide-carrier conjugate comprising a response-inhibiting peptide according to claim 1, conjugated to a macromolecular carrier.

9. A response-inhibiting peptide-carrier conjugate comprising a response-inhibiting peptide according to claim 1, conjugated to a protein carrier.

10. A response-inhibiting peptide-carrier conjugate according to claim 9, wherein the protein carrier is tetanus toxoid.

11. A response-inhibiting peptide-carrier conjugate according to claim 8, wherein the macromolecular carrier is a copolymer of amino acids.

12. A response-inhibiting peptide in accordance with claim 1, having 9–12 amino acid residues.

13. A response-inhibiting peptide in accordance with claim 1, having a sequence selected from the group consisting of SEQ ID NOs. 5, 6, 10, 16, 17 and 18.

14. A response-inhibiting peptide according to claim 4, wherein said peptide differs from amino acid residues 262–266 of SEQ ID NO:2 by one or two of said amino acid substitutions.

15. A response-inhibiting peptide-carrier conjugate in accordance with claim 8, wherein a plurality of said response-inhibiting peptides is conjugated to said macromolecule carrier.

16. A response-inhibiting peptide-carrier conjugate in accordance with claim 9, wherein a plurality of said response-inhibiting peptides is conjugated to said protein carrier.

17. A response-inhibiting peptide in accordance with claim 1, having only a single said amino acid substitution.

18. A response-inhibiting peptide in accordance with claim 17, wherein said myasthenogenic peptide is peptide p195-212 and said amino acid substitution is at amino acid 200, 203, 204, 207 or 208.

19. A response-inhibiting peptide in accordance with claim 17, wherein said myasthenogenic peptide is peptide p259-271 and said amino acid substitution is at amino acid 262, 265 or 266.

20. A response-inhibiting peptide in accordance with claim 1, comprising two linked amino acid sequences wherein the first amino acid sequence includes at least amino acid residues 200–208 of SEQ ID NO:1 and the second amino acid sequence includes at least amino acid residues 262–266 of SEQ ID NO:2, but said sequences of the response-inhibiting peptide differing from SEQ ID NO:1 and SEQ ID NO:2 by one to three amino acid substitutions in each of the SEQ ID NO:1 and NO:2, said substitutions being selected so as to have the function of inhibiting the proliferative response of T lymphocytes from a myasthenia gravis patient to the myasthenogenic peptides of SEQ ID NO:1 and SEQ ID NO:2 to which it corresponds, said substitutions being selected from the group consisting of:

- 201 Ile, 205 Phe, 206 Val, 207 Met, 263 Leu, 264 Ile and 265 Pro being substituted by a different one of any of the amino acids Met, Gly, Ala, Phe, Val, Leu, Ile, Pro or Trp;
- 200 Asp, 202 Thr, 203 Tyr, 204 His, 208 Gln, 262 Glu, and 266 Ser being substituted by a different one of any of the amino acids Glu, Ser, Thr, Tyr, Arg, Lys, His, Asn, Asp or Glu;
- 204 His being substituted with Gly;
- 203 Tyr being substituted with Phe;
- 207 Met being substituted with NLeu; and
- 262 Glu being substituted with Ala.

21. A response-inhibiting peptide in accordance with claim 20, wherein said first and second sequences are linked together by a short stretch of alanine residues.

22. A response-inhibiting peptide in accordance with claim 20, wherein said first and second sequences are linked together by a site for proteolysis by cathepsin.

23. A response-inhibiting peptide in accordance with claim 20, wherein the two amino acid sequences are covalently linked to one another.

24. A response-inhibiting peptide in accordance with claim 23 comprising 25–31 amino acid residues.

25. A response-inhibiting peptide in accordance with claim 23 comprising 31 amino acid residues.

26. A response-inhibiting peptide in accordance with claim 20 comprising SEQ ID NO:17.

27. A response-inhibiting peptide in accordance with claim 20 comprising SEQ ID NO:18.

28. A composition comprising of a response-inhibiting peptide in accordance with claim 20 and a acceptable excipient.

29. A response-inhibiting peptide in accordance with claim 20 having only a single amino acid substitution in each of SEQ ID NO:1 and SEQ ID NO:2.

30. A response-inhibiting peptide in accordance with claim 29, wherein said single amino acid substitutions are in one of the amino acids 200, 203, 204, 207 or 208 of SEQ ID NO:1, and in one of the amino acids 262, 265, or 266 of SEQ ID NO:2.

31. A composition comprising a response-inhibiting peptide in accordance with claim 26 and a pharmaceutically acceptable excipient.

32. A composition comprising a response-inhibiting peptide in accordance with claim 27 and a pharmaceutically acceptable excipient.

33. A response-inhibiting peptide in accordance with claim 20 consisting of one sequence selected from the group consisting of SEQ ID NOs:5 and 6, covalently linked, either directly or by means of a linker peptide, to a sequence selected from the group consisting of SEQ ID NOs:10 and 16.

34. A response-inhibiting peptide of at least nine amino acid residues capable of inhibiting the proliferative response of T lymphocytes from a myasthenia gravis patient to a myasthenogenic peptide corresponding to a sequence of the human acetylcholine receptor α-subunit selected from the group consisting of peptide p195-212 having the formula of SEQ ID NO:1:

```
195                 200                 205
Asp-Thr-Pro-Tyr-Leu-Asp-Ile-Thr-Tyr-His-Phe-

210
Val-Met-Gln-Arg-Leu-Pro-Leu
``` and the peptide p259–271 having the formula of SEQ ID NO:2:

```
      260                 265                 270
Val-Ile-Val-Glu-Leu-Ile-Pro-Ser-Thr-Ser-Ser-Ala-Val
``` said response-inhibiting peptide comprising an amino acid sequence which includes at least amino acid residues 200–208 of SEQ ID NO:1 or amino acid residues 262–266 of SEQ ID NO:2, but differing therefrom by one to three amino acid substitutions, said substitutions being selected so as to have the function of inhibiting the proliferative response of T lymphocytes from a myasthenia gravis patient to the myasthenogenic peptide SEQ ID NO:1 or SEQ ID NO:2 to which it corresponds, said substitutions being selected from the group consisting of: 200, Asp-->Lys; 203, Tyr-->Phe; 204, His-->Gly; 207, Met-->NLeu; 207, Met-->Ala; 208, Gly-->Asp; 208, Gln-->Asn; 262, Glu-->Asp; 262, Glu-->Lys; 262, Glu-->Ser; 262, Glu-->Ala; 265, Pro-->Leu; 265, Pro-->Phe; 266, Ser-->Lys; and 266, Ser-->Asp.

35. A response-inhibiting peptide in accordance with claim 34, comprising two linked amino acid sequences wherein the first amino acid sequence includes at least amino acid residues 200–208 of SEQ ID NO:1 and the second amino acid sequence includes at least amino acid residues 262–266 of SEQ ID NO:2, but said sequences of the response-inhibiting peptide differing from SEQ ID NO:1 and SEQ ID NO:2 by one to three amino acid substitutions in each of the SEQ ID NO:1 and NO:2, said substitutions being selected so as to have the function of inhibiting the proliferative response of T lymphocytes from a myasthenia gravis patient to the myasthenogenic peptides of SEQ ID NO:1 and SEQ ID NO:2 to which it corresponds, said substitutions being selected from the group consisting of: 200, Asp-->Lys; 203, Tyr-->Phe; 204, His-->Gly; 207, Met-->NLeu; 207, Met-->Ala; 208, Gly-->Asp; 208, Gln-->Asn; 262, Glu-->Asp; 262, Glu-->Lys; 262, Glu-->Ser; 262, Glu-->Ala; 265, Pro-->Leu; 265, Pro-->Phe; 266, Ser-->Lys; and 266, Ser-->Asp.

36. A response-inhibiting peptide in accordance with claim 18, wherein said amino acid substitution is a change of 207 Met to Ala.

37. A response-inhibiting peptide in accordance with claim 19, wherein said amino acid substitution is a change of 262 Glu to Lys.

* * * * *

UNITED STATES PATENT AND TRADEMARK OFFICE
CERTIFICATE OF CORRECTION

PATENT NO. : 6,066,621
DATED : May 23, 2000
INVENTOR(S) : Sela et al.

It is certified that error appears in the above-identified patent and that said Letters Patent is hereby corrected as shown below:

Title page,
Under "Other Publications," first column, delete "Roit" and insert therefor -- Roitt --;
Cover page, continuing under "Other Publications," second column, delete "Katz-Levey" and insert therefor -- Katz-Levy --;

Column 6,
Line 61, delete "Glu -->Asp" and insert therefor -- Glu --> Ala--;

Column 14,
Line 60, delete "(580%)" and insert therefor -- (58%) --;

Column 16,
Line 61, delete "40'" and insert therefor -- 4° -- .

Signed and Sealed this

Eleventh Day of September, 2001

Attest:

NICHOLAS P. GODICI
*Attesting Officer*  *Acting Director of the United States Patent and Trademark Office*

UNITED STATES PATENT AND TRADEMARK OFFICE
CERTIFICATE OF CORRECTION

PATENT NO. : 6,066,621
DATED : May 23, 2000
INVENTOR(S) : Sela et al.

It is certified that error appears in the above-identified patent and that said Letters Patent is hereby corrected as shown below:

Title page,
After the section "Related U.S. Application Data", insert the following section:
-- [30] Foreign Application Priority Data
  Dec. 10, 1989 (IL)…..92629 --.

Column 27,
Line 37, before "includes at least", insert -- sequence which --;
Line 50, change "2:08 Gln" to -- 208 Gln --.

Column 29,
Line 44, before "acceptable", insert -- pharmaceutically --.

Signed and Sealed this

Second Day of July, 2002

Attest:

Attesting Officer

JAMES E. ROGAN
*Director of the United States Patent and Trademark Office*